US010779803B2

(12) United States Patent
Prisco et al.

(10) Patent No.: US 10,779,803 B2
(45) Date of Patent: Sep. 22, 2020

(54) DEVICES, SYSTEMS, AND METHODS USING A STEERABLE STYLET AND FLEXIBLE NEEDLE

(71) Applicant: Intuitive Surgical Operations, Inc., Sunnyvale, CA (US)

(72) Inventors: Giuseppe Maria Prisco, Calci (IT); Massimiliano Simi, Leghorn (IT)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 451 days.

(21) Appl. No.: 15/127,811

(22) PCT Filed: Mar. 23, 2015

(86) PCT No.: PCT/US2015/022006
§ 371 (c)(1),
(2) Date: Sep. 21, 2016

(87) PCT Pub. No.: WO2015/153174
PCT Pub. Date: Oct. 8, 2015

(65) Prior Publication Data
US 2017/0095234 A1 Apr. 6, 2017
US 2018/0214138 A9 Aug. 2, 2018

Related U.S. Application Data

(60) Provisional application No. 61/974,113, filed on Apr. 2, 2014.

(51) Int. Cl.
*A61B 10/00* (2006.01)
*A61B 17/00* (2006.01)
(Continued)

(52) U.S. Cl.
CPC ............ *A61B 10/0233* (2013.01); *A61B 1/01* (2013.01); *A61B 10/04* (2013.01); *A61B 17/00* (2013.01);
(Continued)

(58) Field of Classification Search
CPC . A61B 10/0233; A61B 10/04; A61B 17/3478; A61B 2010/0208;
(Continued)

(56) References Cited

U.S. PATENT DOCUMENTS 6,066,125 A * 5/2000 Webster, Jr. ........... A61B 5/015
604/528
8,649,847 B1 * 2/2014 Park .................. A61M 25/0158
600/433
(Continued)

FOREIGN PATENT DOCUMENTS

JP H09276413 A 10/1997
JP 2005528159 A 9/2005
(Continued)

OTHER PUBLICATIONS

Extended European Search Report for Application No. EP15774456.6, dated Feb. 19, 2018, 11 pages.
(Continued)

*Primary Examiner* — Sean P Dougherty
*Assistant Examiner* — David Joseph Fernandez-Fidalgo
(74) *Attorney, Agent, or Firm* — Haynes and Boone, LLP

(57) ABSTRACT

A minimally invasive system comprises an elongate instrument that includes a flexible proximal portion, a rigid distal portion, and a lumen extending from a proximal end to a distal end of the elongate instrument. The lumen defines a longitudinal axis of the elongate instrument. The flexible proximal portion is fixedly coupled to the rigid distal portion. The system further comprises a stylet slidably disposed
(Continued)

within the elongate instrument. The stylet includes a flexible body fixedly coupled to a steerable portion and includes a sensor. The stylet is movable within the elongate instrument between a retracted condition and an extended configuration. A plurality of actuation cables extend through the stylet and terminate in the steerable portion, which comprises a bend-resistive section and a bendable section. The bendable section includes a plurality of articulable segments linked by the actuation cables and includes a plurality of joint pivots disposed between adjacent articulable segments.

20 Claims, 14 Drawing Sheets

(51) Int. Cl.
  A61B 10/02        (2006.01)
  A61B 34/30        (2016.01)
  A61B 17/34        (2006.01)
  A61B 10/04        (2006.01)
  A61B 1/01         (2006.01)
  A61B 34/20        (2016.01)
  A61B 34/35        (2016.01)
  A61B 34/00        (2016.01)
  A61B 1/267        (2006.01)

(52) U.S. Cl.
  CPC .......... *A61B 17/3478* (2013.01); *A61B 34/20* (2016.02); *A61B 34/30* (2016.02); *A61B 34/35* (2016.02); *A61B 34/71* (2016.02); *A61B 1/2676* (2013.01); *A61B 2010/0208* (2013.01); *A61B 2010/045* (2013.01); *A61B 2017/003* (2013.01); *A61B 2034/2051* (2016.02); *A61B 2034/2061* (2016.02); *A61B 2034/2065* (2016.02); *A61B 2034/301* (2016.02)

(58) Field of Classification Search
  CPC ....... A61B 2017/003; A61B 2034/301; A61M 25/0147
  See application file for complete search history.

(56) References Cited

U.S. PATENT DOCUMENTS

| | | | |
|---|---|---|---|
| 2003/0097128 A1 | 5/2003 | Hayzelden | |
| 2004/0133168 A1 | 7/2004 | Salcudean et al. | |
| 2005/0273085 A1 | 12/2005 | Hinman et al. | |
| 2006/0167416 A1* | 7/2006 | Mathis | A61B 10/0275 604/164.01 |
| 2009/0062606 A1* | 3/2009 | Ueda | A61B 1/00154 600/114 |
| 2011/0306836 A1 | 12/2011 | Ohline et al. | |
| 2012/0123395 A1 | 5/2012 | Stoy et al. | |
| 2012/0221007 A1* | 8/2012 | Batten | A61B 17/32056 606/80 |
| 2013/0204124 A1 | 8/2013 | Duindam et al. | |
| 2013/0225997 A1* | 8/2013 | Dillard | A61B 10/0283 600/439 |

FOREIGN PATENT DOCUMENTS

| | | |
|---|---|---|
| JP | 2008501477 A | 1/2008 |
| JP | 2009056054 A | 3/2009 |
| WO | WO-03001986 A2 | 1/2003 |
| WO | WO-2009023779 A1 | 2/2009 |
| WO | WO-2013116140 A1 | 8/2013 |
| WO | WO-2015089372 A1 | 6/2015 |
| WO | WO-2015153174 A1 | 10/2015 |

OTHER PUBLICATIONS

Ayvali E., et al., "Towards a Discretely Actuated Steerable Cannula," IEEE International Conference on Robotics and Automation, May 2012, pp. 1614-1619.
Bassetta E.K., et al., "Design of a Mechanical Clutch-Based Needle-Insertion Device," Proceedings of the National Academy of Sciences, Apr. 2009, vol. 106, pp. 5540-5545.
Bedell C., et al., "Design Optimization of Concentric Tube Robots Based on Task and Anatomical Constraints," IEEE International Conference on Robotics and Automation, May 2011, pp. 398-403.
Borges G.A., et al., "Semi-Automatic Needle Steering System with Robotic Manipulator," IEEE International Conference on Robotics and Automation, May 2012, pp. 1595-1600.
Bruns T.L., et al., "Design of an Autoclavable Active Cannula Deployment Device," Design of Medical Devices Conference, Apr. 2011, 5 pages.
Burdette E.C., et al., "The ACUSITT Ultrasonic Ablator: The First Steerable Needle with an Integrated Interventional Tool," Proceeding SPIE 7629, Medical Imaging Ultrasonic Imaging, Tomography, and Therapy, Mar. 2010, vol. 76290, 10 pages.
Cha H-J., et al., "Master-Slave Robotic System for 3 dimensional Needle Steering," IEEE/RSJ International Conference on Intelligent Robots and Systems, Oct. 2010, pp. 857-862.
Cham M.D., et al., "Lung Biopsy: Special Techniques," Seminars in Respiratory and Critical Care Medicine, 2008, vol. 29(4), pp. 335-349.
Darbemamieh G., et al., "Design and Analysis of a Mechanism for Enhanced Flexibility in Minimally Invasive Surgical Instruments," 5th Cairo International Biomedical Engineering Conference, Dec. 2010, pp. 90-93.
Dimaio S.P., et al., "Needle Insertion Modeling and Simulation," IEEE Transactions on Robotics and Automation, Oct. 2003, vol. 19(5), pp. 864-875.
Dimaio S.P., et al., "Needle Steering and Motion Planning in Soft Tissues," IEEE Transactions on Biomedical Engineering, 2005, pp. 965-974.
Ding J., et al., "Medical Needle Steering for Lung Biopsy: Experimental Results in Tissue Phantoms Using a Robotic Needle Driver," IEEE International Conference on BioInformatics and BioEngineering, 2008, 5 pages.
Dobbelsteen J.V.D., et al., "The Design of a Robotic Actuator for Flexible Needle Steering," 4th Dutch Bio-Medical Engineering Conference , 2013, 2 pages.
Dupont P.E., et al., "Design and Control of Concentric-Tube Robots," IEEE Transactions on Robotics, Apr. 2010, vol. 26(2), pp. 209-225.
Dupont P.E., et al., "Torsional Kinematic Model for Concentric Tube Robots," IEEE International Conference on Robotics and Automation, Kobe International Conference Center, May 2009, pp. 3851-3858.
Figueredo S.L.,, "Design of an Endoscopic Biopsy Needle With Flexural Members," ASME Journal of Medical Devices, Sep. 2006, 97 pages.
Frasson L., et al., "Experimental Evaluation of a Novel Steerable Probe with a Programmable Bevel Tip Inspired by Nature," Journal of Robotic Surgery, 2012, vol. 6, pp. 189-197.
Gahler M., et al., "Fiber Bragg Grating based Force Sensing Needle," Department of BioMechanical Engineering, Delft University of Technology, 1 page.
Goksel O., et al., "Modeling and Simulation of Flexible Needles," Medical Engineering and Physics, 2009, vol. 31, pp. 1069-1078.
Gosline A.H., et al., "Metal MEMS Tools for Beating-heart Tissue Removal," IEEE International Conference on Robotics and Automation, May 2012, pp. 1921-1926.
Graves C.M., et al., "Towards a Compact Robotically Steerable Thermal Ablation Probe," IEEE International Conference on Robotics and Automation, May 2012, pp. 709-714.

(56) References Cited

OTHER PUBLICATIONS

Heiden V.D., et al., "Accurate and Efficient Fiber Optical Shape Sensor for MRI Compatible Minimally Invasive Instruments," Proceeding of SPIE, Optical Systems Design, 2012, vol. 8550, pp. 85500L-1to 85500L-14.
Henken K., et al., "Accuracy of Needle Position Measurements using Fiber Bragg Gratings," Minimally Invasive Therapy and Allied Technologies, 2012, vol. 21(6), pp. 408-414.
Henken K., et al., "Sensorized Steerable Needle," 4th Dutch Bio-Medical Engineering Conference, 2013, 2 pages.
Henken K., et al., "Steerable Needle with Shape Sensing for MR-Guided Interventions," Delft University of Technology, 1 page.
Henken K.R., et al., "Strain Sensor Configurations for Needle Tip Position Estimation," Delft University of Technology (Poster), 1 page.
International Preliminary Report on Patentability for Application No. PCT/US15/22006, dated Oct. 13, 2016, 13 pages.
International Search Report and Written Opinion for Application No. PCT/US15/22006, dated Jul. 9, 2015, 18 pages.
Jelinek F., et al., "Dragonflex—Smart and Simple Steerable Laparoscopic Instrument," 4th Dutch Bio-Medical Engineering Conference , 2013, 2 pages.
Kallem V., et al., "Image Guidance of Flexible Tip-Steerable Needles," IEEE Transactions on Robotics, Feb. 2009, pp. 191-196.
Kalvoy H., et al., "Needle Position Determined by Tissue Impedance," 13th International Conference on Electrical Bioimpedance and the 8th Conference on Electrical Impedance Tomography, 2007, pp. 205-208.
Kemp M.,, "Flexible Needle Steering using Fiber Bragg Grating Sensors," University of Twente, EEMCS / Electrical Engineering Control Engineering, Aug. 2012, 43 pages.
Khoorjestan S.M., et al., "Design and Modeling of a Novel Flexible Surgical Instrument Applicable in Minimally Invasive Surgery," International Journal of Natural and Engineering Sciences, 2010, vol. 4 (1), pp. 53-60.
Ko S.Y., et al., "Towards a Miniaturized Needle Steering System with Path Planning for Obstacle Avoidance," IEEE Transactions on Biomedical Engineering, 2012, 8 pages.
Ko S.Y., et al., "Two-Dimensional Needle Steering with a Programmable Bevel Inspired by Nature: Modeling Preliminaries," IEEE/RSJ International Conference on Intelligent Robots and Systems, Oct. 2010, pp. 2319-2324.
Koseki Y., et al., "Coaxial Needle Insertion Assistant for Epidural Puncture," International Conference on Instrumentation Control and Automation, 2011, 6 pages.
Kratchman L.B et al., "Toward Robotic Needle Steering in Lung Biopsy: A Tendon-Actuated Approach," Medical Imaging , 2011, 8 pages.
Lock J et al., "Friction Modeling in Concentric Tube Robots," IEEE International Conference on Robotics and Automation, Shanghai International Conference Center, May 2011, pp. 1139-1146.
Mahvash M., et al, "Fast Needle Insertion to Minimize Tissue Deformation and Damage," IEEE International Conference on Robotics and Automation, Kobe International Conference Center, May 2009, pp. 3097-3102.
Mahvash M et al., "Mechanics of Dynamic Needle Insertion into a Biological Material," IEEE Transactions on Biomedical Engineering, Apr. 2010, vol. 57(4), pp. 934-943.
Mahvash M et al., "Stiffness Control of Surgical Continuum Manipulators," IEEE Transactions on Robotics, Apr. 2010, vol. 27(2), pp. 334-345.
Mahvash M et al., "Toward a Hybrid Snake Robot for Single-Port Surgery," 33rd Annual International Conference of the IEEE EMBS, 2011, pp. 5372-5375.
Majewicz A., et al., "Behavior of Tip-Steerable Needles in Ex Vivo and In Vivo Tissue," IEEE Transactions on Biomedical Engineering, Oct. 2012, vol. 59(10), pp. 2705-2715.
Misra S., et al., "Mechanics of Flexible Needles Robotically Steered through Soft Tissue," The International Journal of Robotics Research, 2010, vol. 29(13), pp. 1640-1660.

Okamura A.M., et al., "Evaluation of Robotic Needle Steering in ex vivo Tissue," IEEE International Conference on Robotics and Automation, May 2010, pp. 2068-2073.
Okamura A.M., et al., "Force Modeling for Needle Insertion Into Soft Tissue," IEEE Transactions on Biomedical Engineering, Oct. 2004, vol. 51(10), pp. 1707-1716.
Okamura A.M., et al., "Modeling and Control of Needles With Torsional Friction," IEEE Transactions on Biomedical Engineering, Dec. 2009, vol. 56(12), pp. 2905-2916.
Okamura A.M., et al., "Needle-Tissue Interaction Forces for Bevel-Tip Steerable Needles," Proceedings of the 2nd Biennial IEEE/RAS-EMBS International Conference on Biomedical Robotics and Biomechatronics, Oct. 2008, pp. 224-231.
Okazawa S., et al., "Hand-Held Steerable Needle Device," IEEE/ASME Transactions on Mechatronics, Jun. 2005, vol. 10(3), pp. 285-296.
Park YL., et al., "MRI-Compatible Haptics: Feasibility of using Optical Fiber Bragg Grating Strain-Sensors to Detect Deflection of Needles in an MRI Environment," International Society for Magnetic Resonance in Medicine, May 2008, 1 page.
Park YL., et al., "Real-Time Estimation of 3-D Needle Shape and Deflection for MRI-Guided Interventions," IEEE/ASME Transactions on Mechatronics, Dec. 2010, vol. 15(6), pp. 906-915.
Patel R.V., et al., "Robot-Assisted Needle Steering Using a Control Theoretic Approach," Journal of Intelligent and Robotic Systems, DOI 10.1007/s10846-010-9455-2, 2011, vol. 62, pp. 397-418.
Riviere C.N., et al., "Flexible Needle Steering System for Percutaneous Access to Deep Zones of the Brain," IEEE 32nd Annual Northeast Bioengineering Conference, 2006, pp. 103-104.
Roesthuis R.J et al., "Mechanics of Needle-Tissue Interaction," IEEE/RSJ International Conference on Intelligent Robots and Systems, Sep. 2011, pp. 2557-2563.
Rucker D.C., et al., "A Geometrically Exact Model for Externally Loaded Concentric-Tube Continuum Robots," IEEE Transactions on Robotics, Oct. 2010, vol. 26(5), pp. 769-780.
Rucker D.C., et al., "Mechanics of Bending, Torsion, and Variable Precurvature in Multi-Tube Active Cannulas," IEEE International Conference on Robotics and Automation, May 2009, pp. 2533-2537.
Rucker D.C., et al., "Parsimonious Evaluation of Concentric-Tube Continuum Robot Equilibrium Conformation," IEEE Transactions on Biomedical Engineering, Sep. 2009, vol. 56(9), pp. 2308-2311.
Sadjadi H., et al., "Needle Deflection Estimation using Fusion of Electromagnetic Trackers," 34th Annual International Conference of the IEEE, 2012, pp. 952-955.
Sears P., et al., "A Steerable Needle Technology Using Curved Concentric Tubes," Proceedings of the 2006 IEEE/RSJ International Conference on Intelligent Robots and Systems, Oct. 2006, pp. 2850-2856.
Sears P., et al., "Inverse Kinematics of Concentric Tube Steerable Needles," IEEE International Conference on Robotics and Automation, Apr. 2007, pp. 1887-1892.
Su H., et al., "A Miniature MRI-Compatible Fiber-optic Force Sensor Utilizing Fabry-Perot Interferometer," SEM Annual Conference & Exposition on Experimental and Applied Mechanics, 2011, 6 pages.
Su H., et al., "A MRI-Guided Concentric Tube Continuum Robot with Piezoelectric Actuation: A Feasibility Study," IEEE International Conference on Robotics and Automation, 2012, pp. 1939-1945.
Su H., et al., "Real-time MRI-Guided Needle Placement Robot with Integrated Fiber Optic Force Sensing," IEEE International Conference on Robotics and Automation, May 2011, pp. 1583-1588.
Swaney P.J., et al., "A Flexure-Based Steerable Needle: High Curvature with Reduced Tissue Damage," IEEE Transactions on Biomedical Engineering, 2013, 4 pages.
Swensen J.P., et al., "Torsional Dynamics Compensation Enhances Robotic Control of Tip-Steerable Needles," IEEE International Conference on Robotics and Automation, May 2012, pp. 1601-1606.
Torres L.G et al., "Task-oriented Design of Concentric Tube Robots using Mechanics-based Models," 2012, 7 pages.

(56) References Cited

OTHER PUBLICATIONS

Van Gerwen D.J., et al., "Needle-Tissue Interaction Forces—A Survey of Experimental Data," Medical Engineering and Physics, 2012, vol. 34, pp. 665-680.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Vrooijink G., et al., "Three-Dimensional Flexible Needle Steering using Two-Dimensional Ultrasound Images," 4th Dutch Bio-Medical Engineering Conference, 2013, 3 pages.
Walsh C.J et al., "Design of a Robotic Tool for Percutaneous Instrument Distal Tip Repositioning," 33rd Annual International Conference of the IEEE EMBS, Sep. 2011, pp. 2097-2100.
Webster R.J., et al., "Design Considerations for Robotic Needle Steering," Proceedings of IEEE International Conference on Robotics and Automation, Apr. 2005, pp. 3588-3594.
Webster R.J., et al., "Kinematics and Calibration of Active Cannulas," IEEE International Conference on Robotics and Automation, May 2008, pp. 3888-3895.
Webster R.J., et al., "Mechanics of Precurved-Tube Continuum Robots," IEEE Transactions on Robotics, Feb. 2009, vol. 25(1), pp. 67-78.
Webster R.J., et al., "Toward Active Cannulas: Miniature Snake-Like Surgical Robots," Proceedings of IEEE/RSJ International Conference on Intelligent Robots and Systems, Oct. 2006, pp. 2857-2863.
Partial Supplementary European Search Report for Application No. EP15774456.6, dated Nov. 8, 2017, 13 pages.

\* cited by examiner

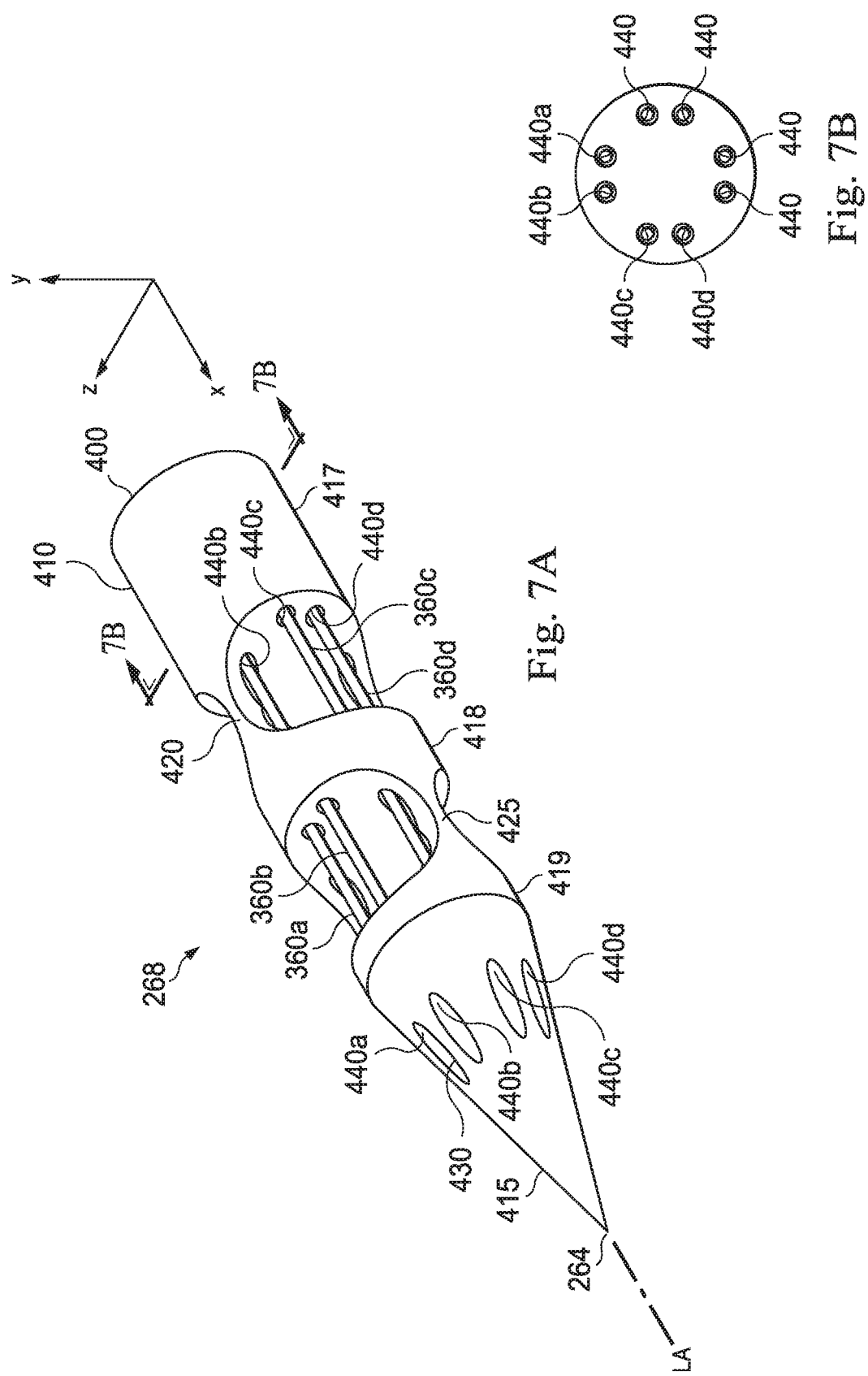

DEVICES, SYSTEMS, AND METHODS USING A STEERABLE STYLET AND FLEXIBLE NEEDLE

RELATED APPLICATIONS

This patent application is the U.S. national phase of International Application No. PCT/US15/22006, filed Mar. 23, 2015, which designated the U.S. and claims priority to and the benefit of the filing date of U.S. Provisional Patent Application 61/974,113, titled "Devices, Systems, and Methods Using a Steerable Stylet and Flexible Needle," filed Apr. 2, 2014, which are incorporated by reference herein in their entirety.

FIELD

The present disclosure is directed to systems and methods for navigating a patient anatomy to conduct a minimally invasive procedure, and more particularly to apparatus and methods for obtaining a targeted tissue biopsy using a low-profile, flexible, steerable stylet and needle assembly.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Clinicians may insert medical tool through these natural orifices or incisions to reach a target tissue location. Medical tools include instruments such as therapeutic instruments, diagnostic instruments, and surgical instruments. To reach the target tissue location, a minimally invasive medical tool may navigate natural or surgically created passageways in anatomical systems such as the lungs, the colon, the intestines, the kidneys, the heart, the circulatory system, or the like.

Minimally invasive medical procedures typically rely on some sort of instrument position monitoring to ensure proper access to, and behavior at, the target tissue location. Conventional minimally invasive medical instruments are generally either formed from generally rigid, elongate elements (e.g., laparoscopic or robotic systems) or highly flexible systems designed to follow a predetermined anatomic path (e.g., angioplasty balloon catheters). In either case, position monitoring typically involves localized tracking of a discrete portion of the instrument (e.g., the distal tip of a catheter). The remaining guidewire/catheter length is not actively monitored, except in an incidental sense to the extent the remaining length is shown during fluoroscopic visualization of the tip advancement.

However, increasingly more complex minimally invasive surgical systems can require enhanced instrument position monitoring for safe and effective use. For example, the development of flexible, steerable needles provides an opportunity for procedures such as biopsy and/or therapeutic treatment, such as ablation treatments or radioactive seeds placement, at internal locations that would be problematic to access via a straight path (e.g., in situations where it would be undesirable to puncture any intervening anatomy). Flexible, steerable needles can be delivered to the target site by direct penetration into the tissue, such as for example in the case of transcutaneous biopsy needles for the liver or other internal organs. In other instances, flexible, steerable needles can be delivered to the target site through the lumen of an endoscope or a catheter, such as for example in the case of transluminal lung or stomach biopsies.

The use and positional tracking of a flexible needle in a minimally invasive fashion can be significantly more complicated than conventional robotic or laparoscopic procedures. Not only is the variability in the actual shape of a steerable needle much greater than that of a linkage of rigid elements, but the needle flexibility and tip geometry can greatly increase susceptibility to deviation from a target trajectory due to variations in tissue characteristics (e.g., scar tissue, or otherwise denser than expected tissue, may result in greater than expected curvature of the flexible needle). In particular, during insertion through tissue, flexible needles can be passively steered through tissue because of lateral forces applied by the tissue on the often asymmetric or beveled needle tip. As the flexible needle shaft follows behind the tip, both the needle tip and the needle shaft may be deflected from the intended course. Thus, accurately guiding and tracking the position of a flexible needle poses unique difficulties.

In addition, many steerable needles have a greater outer diameter than may be desirable in certain applications. For endoluminal needles in particular, a small outer diameter is desirable to ensure their smooth passage through scope channels.

Accordingly, it is desirable to provide a steerable, flexible needle system that can be effectively guided and tracked during minimally invasive medical procedures. The devices, systems, and methods disclosed herein overcome one or more of the deficiencies of the prior art.

SUMMARY

The embodiments of the invention are summarized by the claims that follow the description.

In one embodiment, the present disclosure describes a minimally invasive system comprising an elongate instrument and a stylet slidably disposed within a lumen of the elongate instrument. The elongate instrument extends from a proximal end to a distal end. In one aspect, the instrument includes a flexible proximal portion and a rigid distal portion. In one aspect, the flexible proximal portion is fixedly coupled to the rigid distal portion. In one aspect, a lumen extends from the proximal end to the distal end through the flexible proximal portion and the rigid distal portion to define a longitudinal axis of the instrument. In one aspect, the stylet includes a flexible body fixedly coupled to a steerable portion and a sensor element extending through the flexible body. In one aspect, the stylet is movable within the elongate instrument between a retracted condition in which the steerable portion is retracted within the elongate instrument and an extended configuration in which the steerable portion at least partially extends from the rigid distal portion of the elongate instrument.

In another embodiment, the present disclosure describes a minimally invasive system comprising an actuator, a needle, a stylet, and a plurality of actuation cables. The needle includes a lumen extending from a proximal end to a distal end and defining a longitudinal axis of the instrument. The stylet can be positioned within the lumen of the elongate instrument. In one aspect, the stylet includes a proximal flexible body, a distal steerable portion, and a sensor element extending through the flexible body. In one aspect, the distal steerable portion includes a bend-resistive tip. In one aspect, the stylet is movable within the needle between a retracted condition in which the steerable portion is retracted within the lumen of the needle and an extended configuration in which the steerable portion of the medical instrument at least partially extends from the distal end of the needle. In one aspect, the plurality of actuation cables extends from the actuator through the flexible body of the stylet and terminates in the steerable portion of the stylet.

In another embodiment, the present disclosure describes a method of evaluating a target area in a patient. In one aspect, the method comprises advancing a needle system into the patient toward the target area. In one aspect, the needle system comprises a stylet slidably positioned within a lumen of an elongate medical instrument, and the stylet includes a flexible body, a distal steerable portion, and a sensor element configured to detect characteristics of the stylet. In one aspect, the method includes advancing the steerable portion of the stylet distal to a distal end of the elongate medical instrument, and acquiring characteristics of the stylet from the sensor element as the stylet advances toward the target area. In one aspect, the method includes determining a position of the stylet and the elongate medical instrument relative to the target area based on the acquired characteristics. In one aspect, the method includes steering the steerable portion of the stylet toward the target area based on the determined position, and advancing the elongate medical instrument over the stylet into the target area.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 3A illustrates an exemplary needle comprising discrete links, FIG. 3B illustrates an exemplary needle comprising a continuous sheath, and FIG. 3C illustrates an exemplary needle comprising a coiled tube.

FIG. 7A illustrates a perspective view of an exemplary steerable portion of the sensor stylet shown in FIG. 5 in an unbent condition accordance with an embodiment of the present disclosure.

Figure 8A:
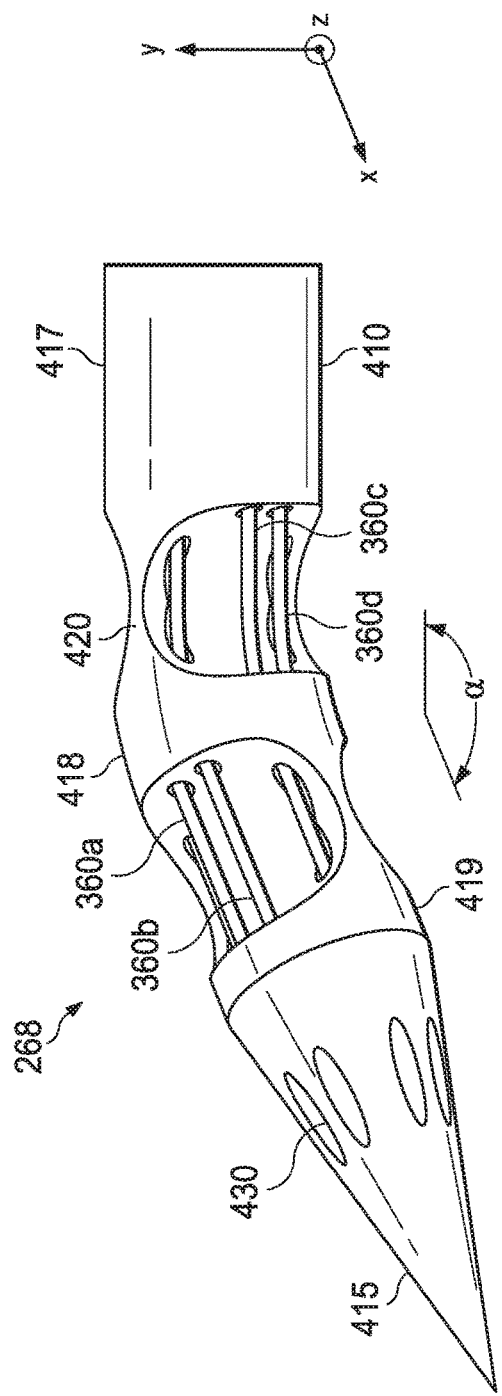
Figure 8B:
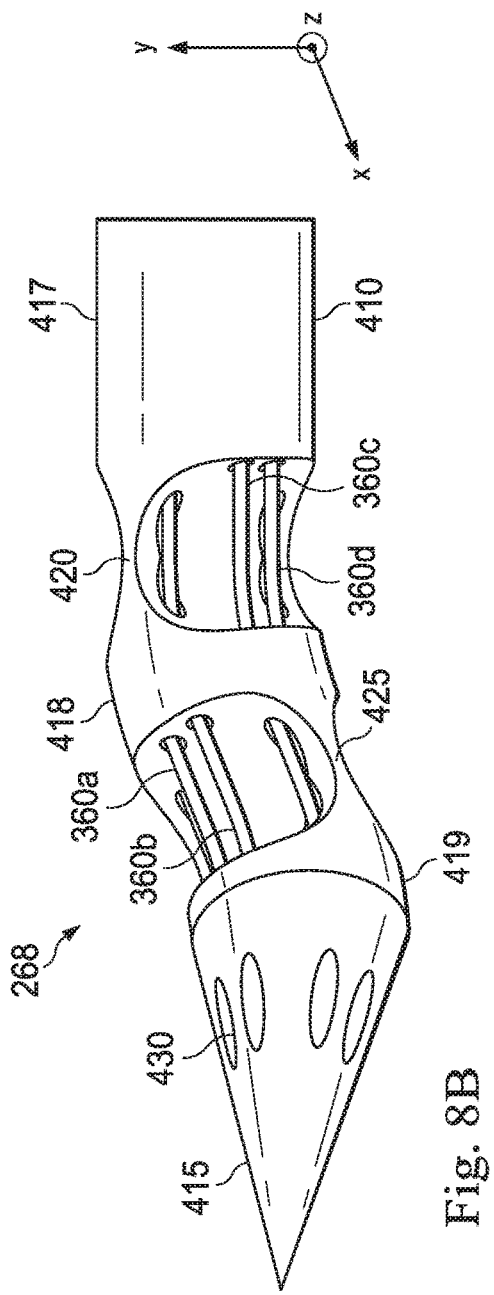

FIG. 7B illustrates a cross-sectional view of the exemplary steerable portion shown in FIG. 7A in accordance with an embodiment of the present disclosure FIGS. 8A and 8B illustrate perspective views of the exemplary steerable portion shown in FIG. 7A in bent conditions in accordance with the present disclosure. FIG. 8A illustrates the exemplary steerable portion bent at an exemplary proximal joint pivot, and FIG. 8B illustrates the exemplary steerable portion bent at an exemplary proximal joint pivot and at an exemplary distal joint pivot.

Figure 9:
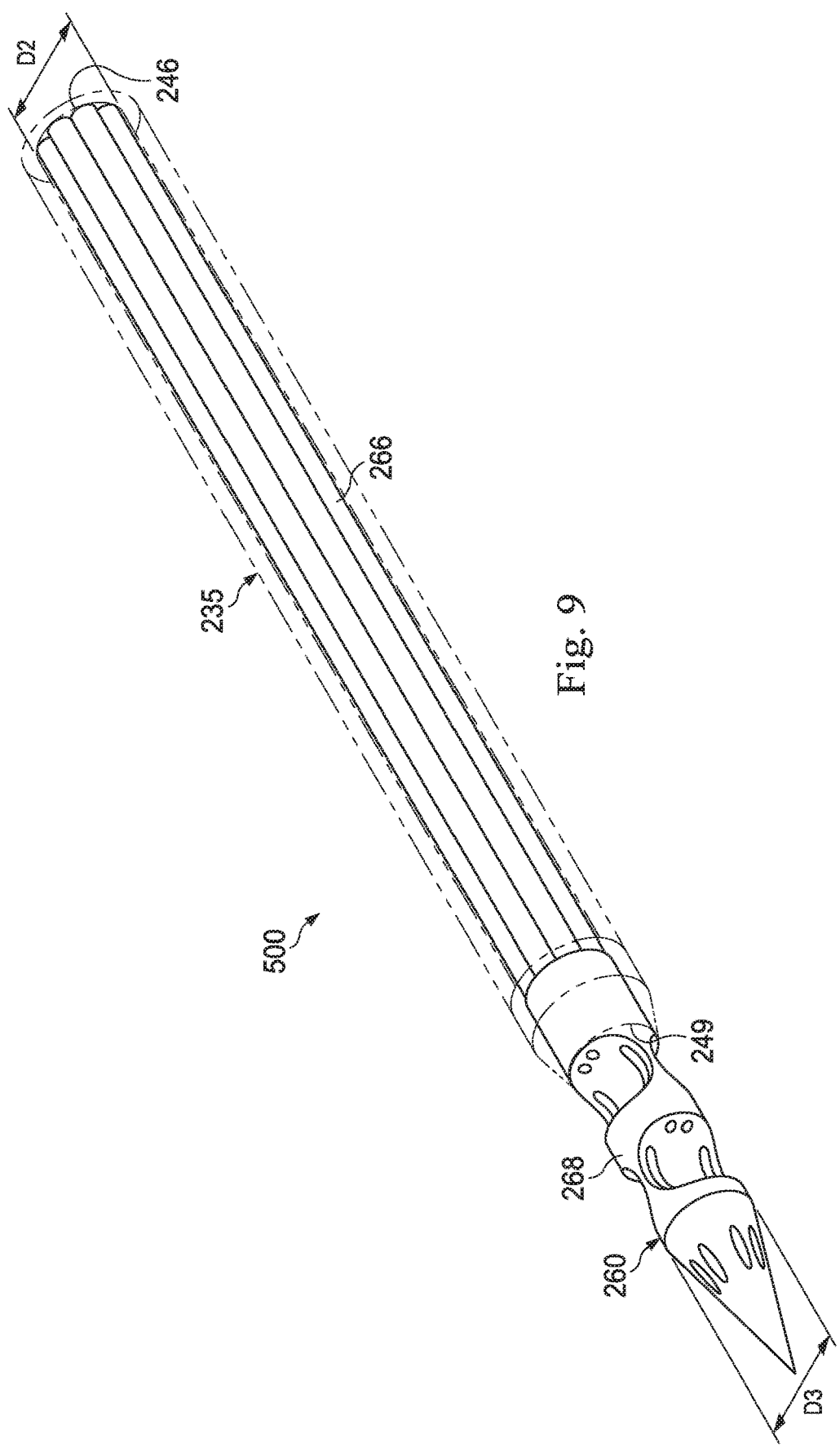

FIG. 9 illustrates a perspective view of an exemplary needle system according to one embodiment of the present disclosure. In particular, FIG. 9 illustrates the exemplary sensor stylet shown in FIG. 5 positioned within and extending from the exemplary needle shown in FIG. 4 according to the present disclosure.

Figure 10:
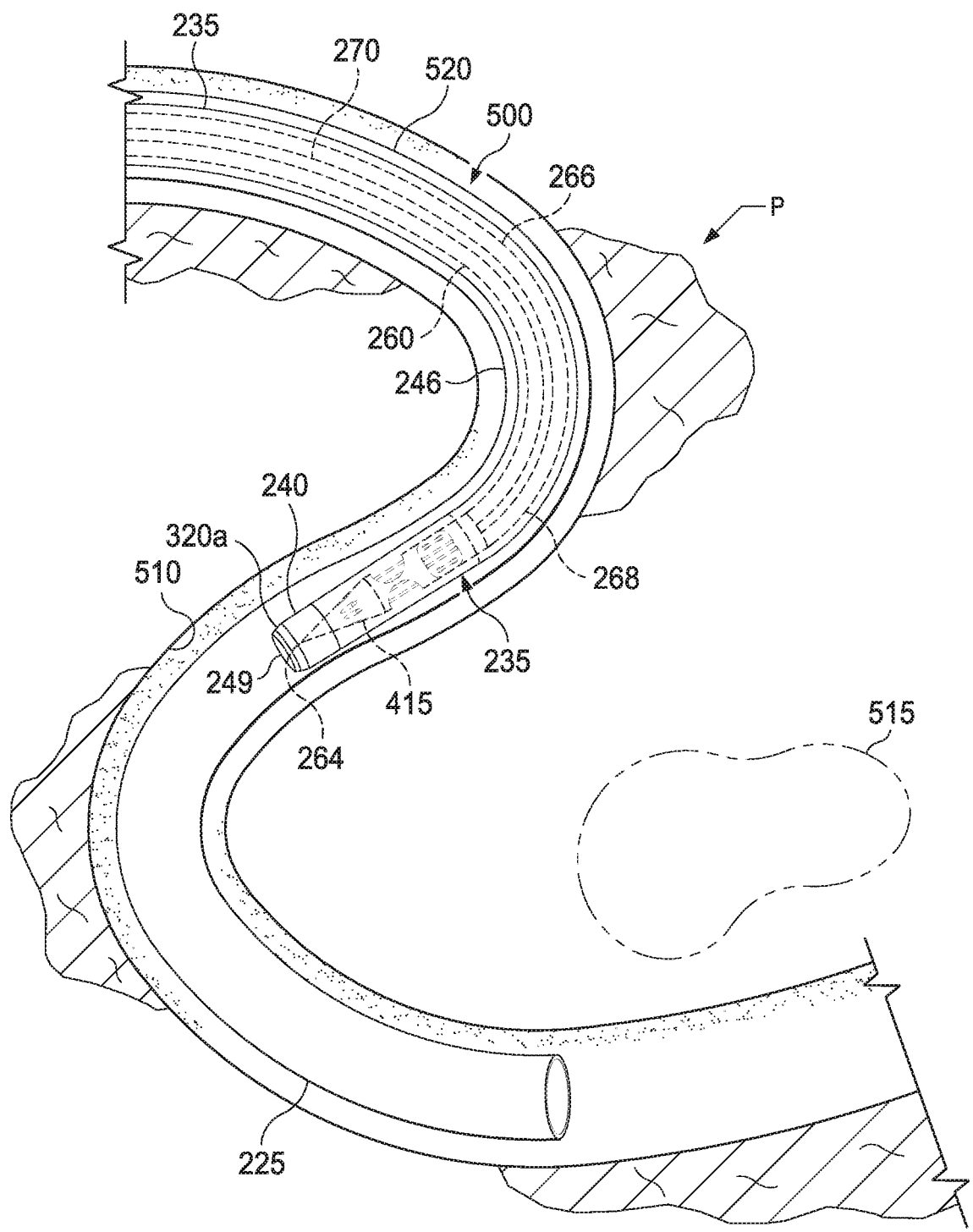

FIG. 10 illustrates a diagrammatic view of the exemplary needle system shown in FIG. 9 navigating a tortuous pathway (i.e., within a patient's anatomy) in accordance with an embodiment of the present disclosure.

Figure 11:
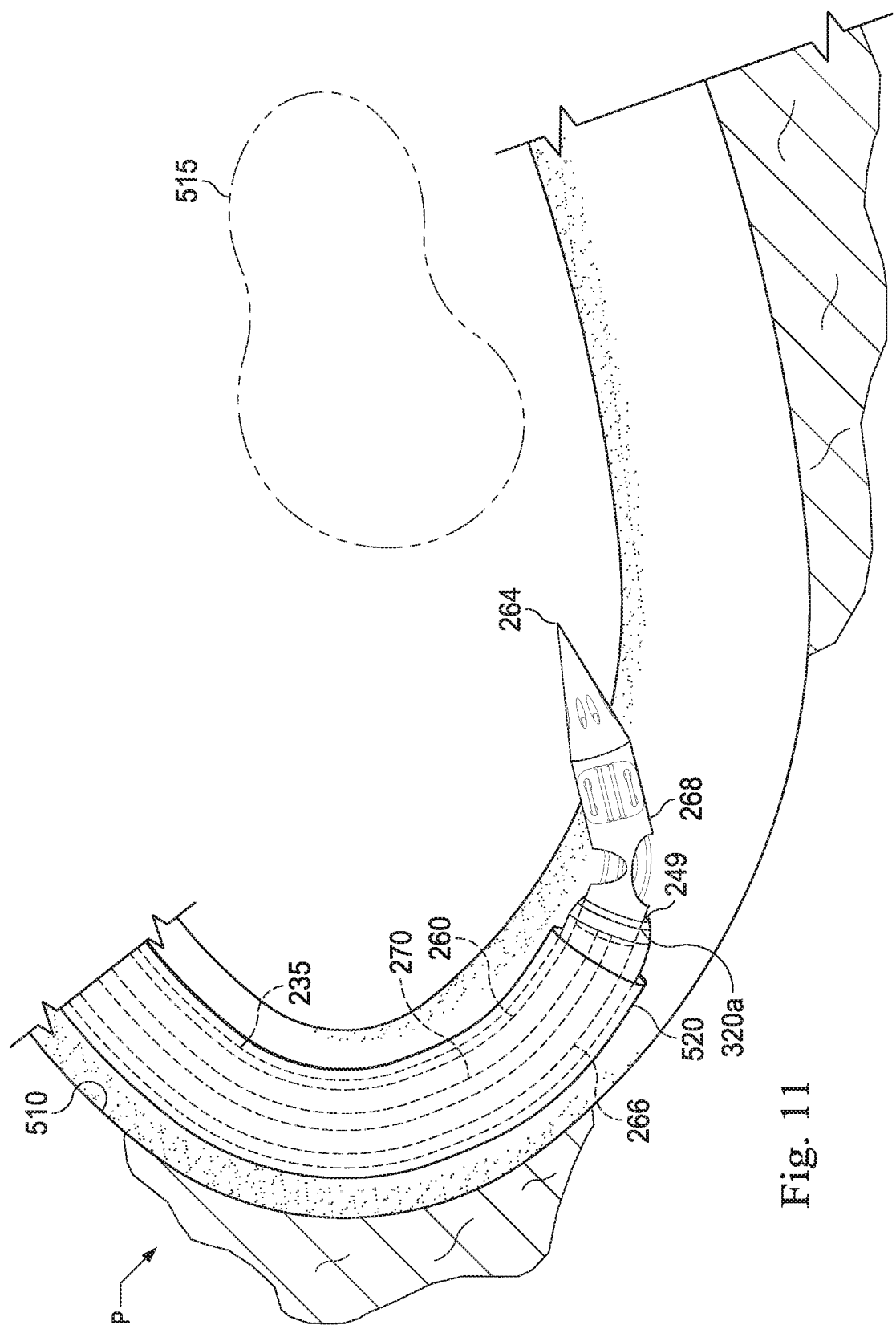

FIG. 11 illustrates a diagrammatic view of the exemplary needle system shown in FIG. 9 steering toward a target area in accordance with an embodiment of the present disclosure.

Figure 12:
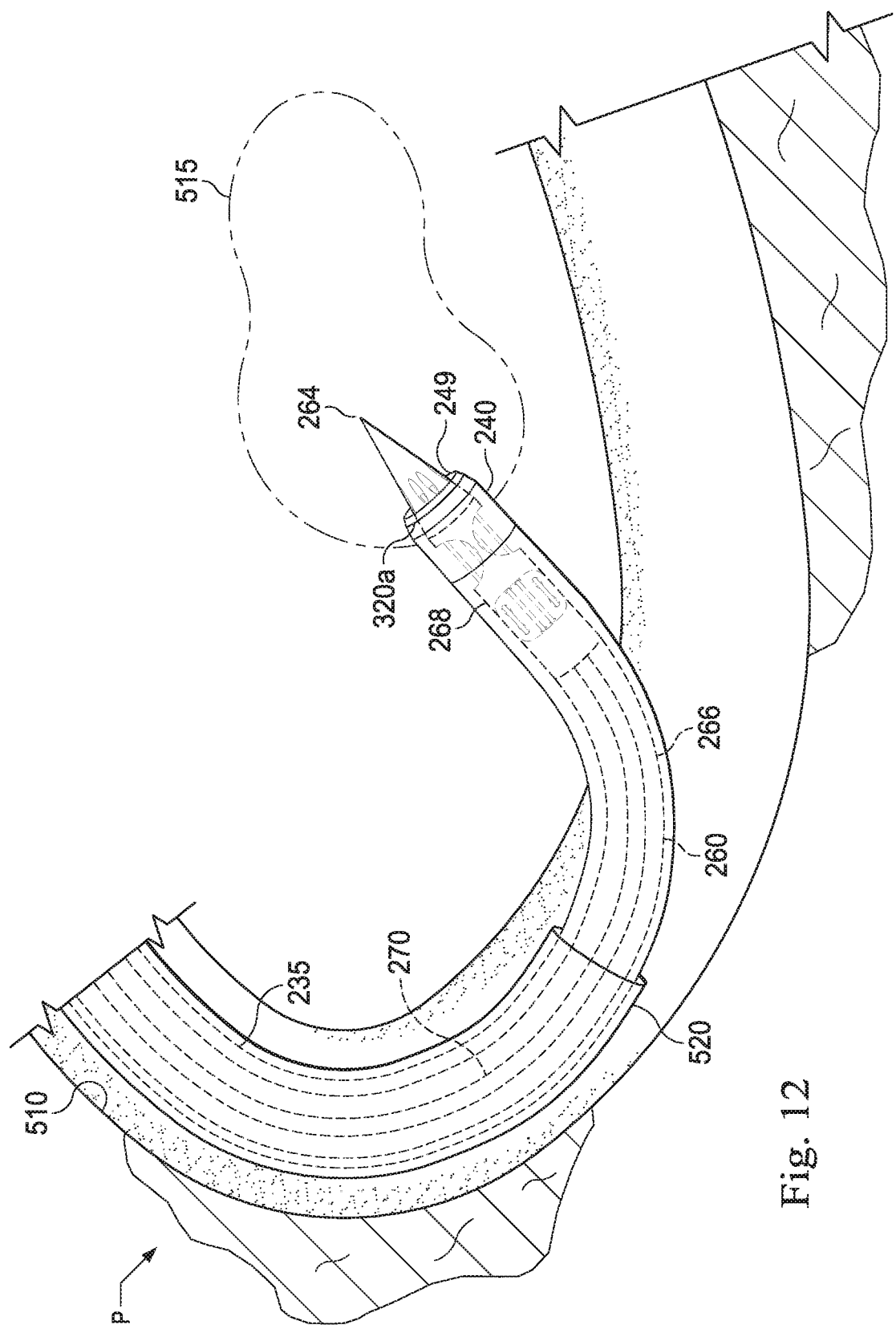

FIG. 12 illustrates a diagrammatic view of the exemplary needle system shown in FIG. 9 as the exemplary needle advances over the exemplary sensor stylet.

Figure 13:
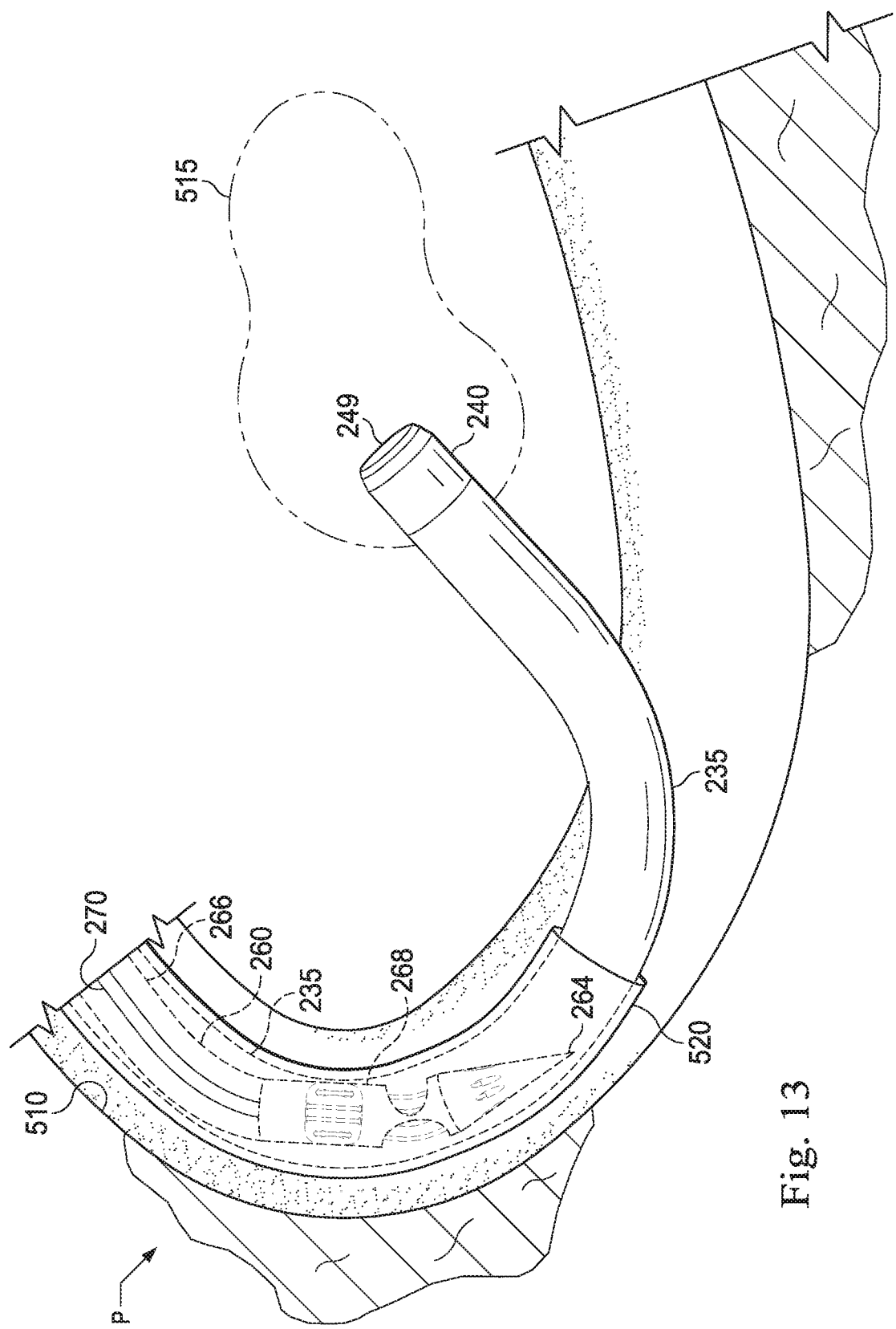

FIG. 13 illustrates a diagrammatic view of the exemplary needle system shown in FIG. 9 obtaining a biopsy from the target area in accordance with an embodiment of the present disclosure.

Figure 14:
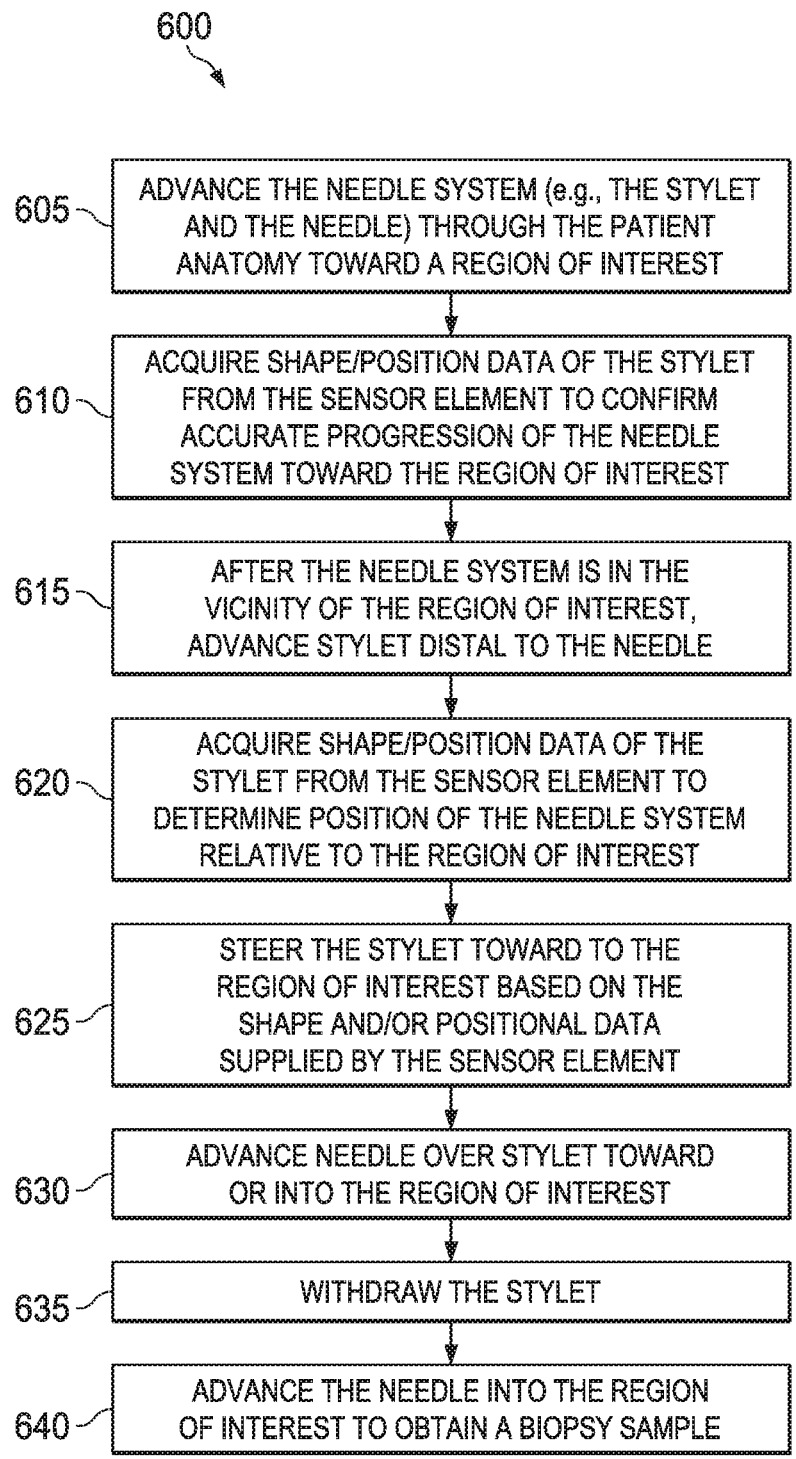

FIG. 14 is a flowchart illustrating an exemplary method of using an exemplary sensor stylet in accordance with an embodiment of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments.

For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

It will be appreciated that the terms "proximal" and "distal" are used herein with reference to a clinician manipulating an end of an instrument extending from the clinician to a surgical site. The term "proximal" refers to the portion of the instrument closer to the clinician, and the term "distal" refers to the portion of the instrument further away from the clinician and closer to the surgical site. For conciseness and clarity, spatial terms such as "horizontal," "vertical," "above," and "below" may be used herein with respect to the drawings. However, surgical instruments are used in many orientations and positions, and there terms are not intended to be limiting and absolute.

The present disclosure relates generally to steerable, flexible needle systems used in minimally invasive medical procedures, including without limitation diagnostic, surgical, and/or therapeutic procedures. In some instances, embodiments of the present disclosure are configured to be part of a teleoperational system. Those of skill in the art will realize that the steerable, flexible needle systems disclosed herein may be utilized in similar (e.g., non-teleoperational) applications requiring a steerable, flexible needle system.

The needle systems disclosed herein comprise an actively steerable stylet configured to guide a flexible medical instrument such as, by way of nonlimiting example, a flexible needle. The flexible instruments and steerable stylets disclosed herein are arranged in a telescoping fashion to allow the instrument to advance distally over the stylet as or after the stylet advances into tissue. The actively steerable stylets can act as inner guides for the flexible instrument as it navigates through anatomical tissue. In one aspect, the needle systems disclosed herein are configured to include position/shape sensors that extend axially along the length of the stylet and terminate at or proximate to the stylet tip. The stylets disclosed herein may be configured to minimize the bending strain on the sensors as well as support and guide the needle during insertion and progression through anatomical tissue. These features of the needle systems disclosed herein may enhance the precision, steerability, stability, and distance/trajectory control of a needle during insertion in a minimally invasive procedure. Thus, the needle systems disclosed herein may improve the performance of flexible needles, and may increase the range of suitable applications for flexible needles (and, in particular, flexible endoscopic needles). For example, in one instance, the flexible needle systems disclosed herein may enable the user to more accurately reach and sample a target biopsy location, more easily navigate around critical structures, and decrease the chance of inaccurate biopsies.

Figure 1:
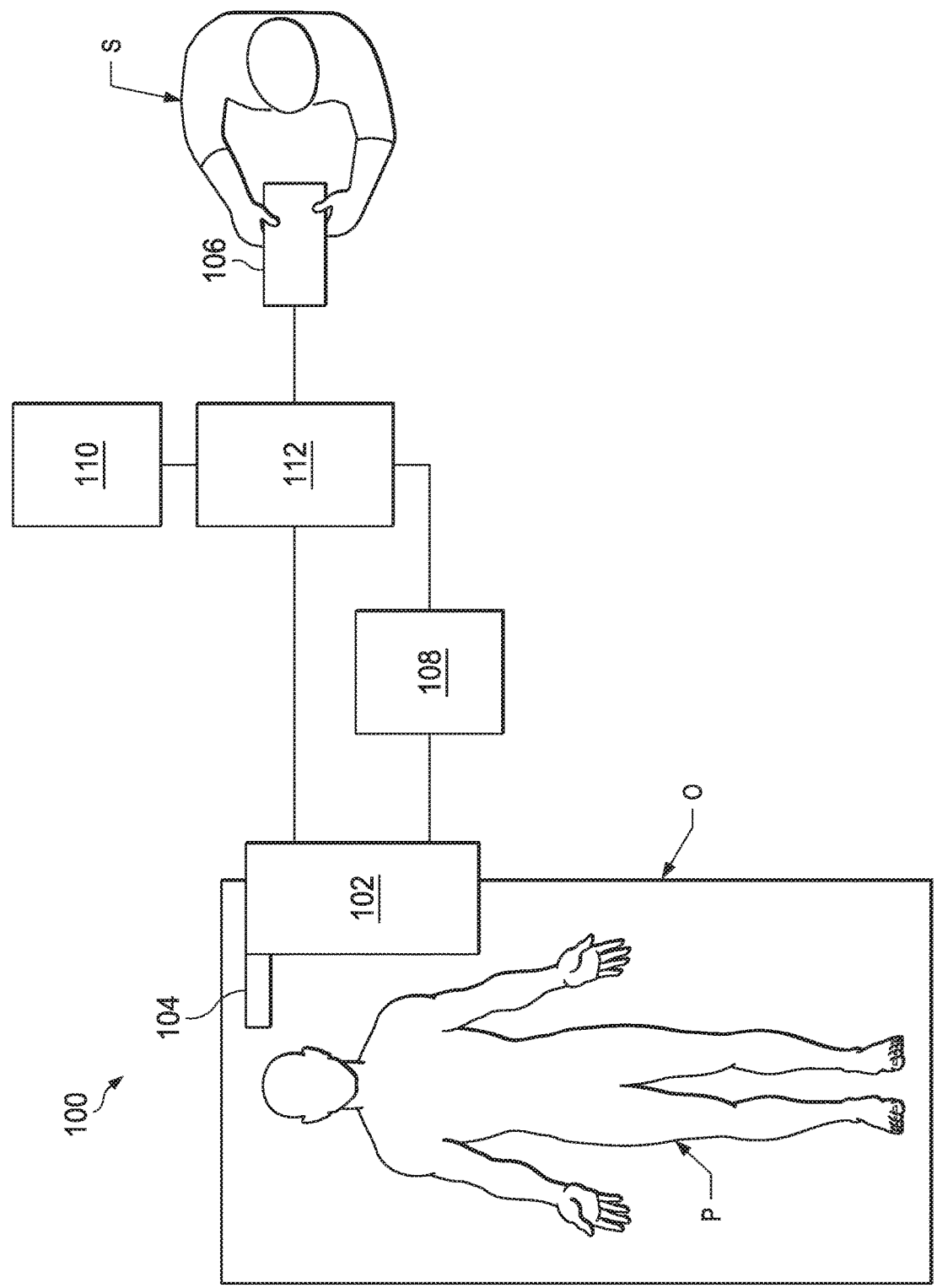
FIG. 1 illustrates a teleoperational medical system in accordance with an embodiment of the present disclosure.

According to various embodiments, medical procedures, such as biopsy procedures, may be performed using a teleoperational system to guide instrument delivery. Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 100 generally includes a teleoperational assembly 102 mounted to or near an operating table O on which a patient P is positioned. A medical instrument system 104 is operably coupled to the teleoperational assembly 102. An operator input system 106 allows a surgeon or other type of clinician S to view images of or representing the surgical site and to control the operation of the medical instrument system 104.

The operator input system 106 may be located at a surgeon's console, which is usually located in the same room as operating table O. It should be understood, however, that the surgeon S can be located in a different room or a completely different building from the patient P. Operator input system 106 generally includes one or more control device(s) for controlling the medical instrument system 104. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device (s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of motors that drive inputs on the medical instrument system 104. These motors move in response to commands from the control system (e.g., a control system 112). The motors include drive systems which when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

Alternatively or additionally, display system 110 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intra-operative images may include two-dimensional, three-dimensional, or four-dimensional (including e.g., time based or velocity based information) images and associated image data sets for reproducing the images.

In some embodiments, the display system 110 may display a virtual visualization image in which the actual location of the medical instrument is registered (e.g., dynamically referenced) with preoperative or concurrent images to present the surgeon with a virtual image of the internal surgical site at the location of the distal end of the medical instrument.

In other embodiments, the display system 110 may display a virtual visualization image in which the actual location of the medical instrument is registered with prior images (including preoperatively recorded images) or concurrent images to present the surgeon with a virtual image of a medical instrument at the surgical site. An image of a portion of the medical instrument system 104 may be superimposed on the virtual image to assist the surgeon controlling the medical instrument.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intra-operatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image- Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 2:
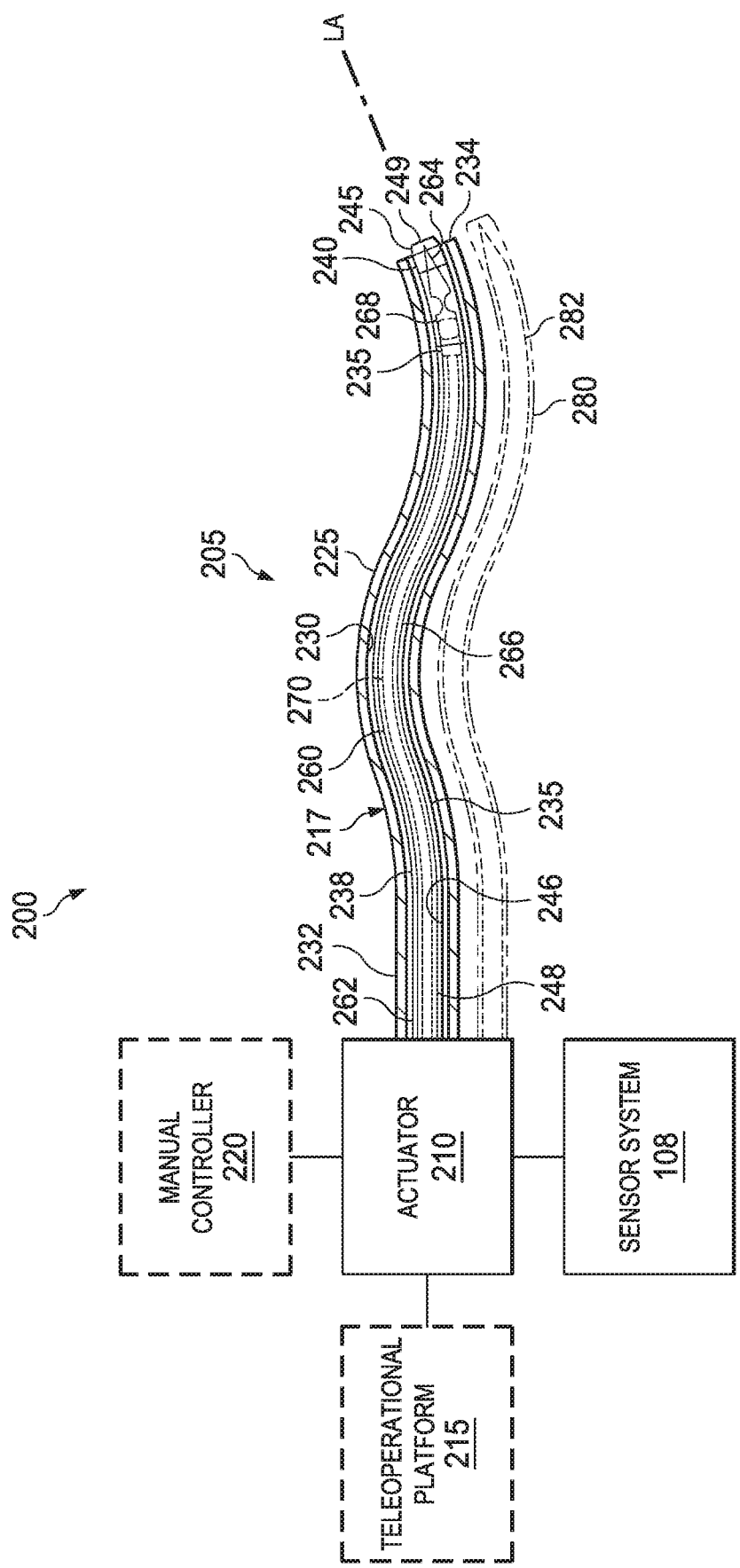
FIG. 2 illustrates a block diagram of a medical system including an exemplary needle system in accordance with an embodiment of the present disclosure.

FIG. 2 illustrates a medical instrument system 200 that includes an exemplary needle system 205, an actuator 210, and the sensor system 108. The needle system 205 may be the same as the medical instrument system 104 of the teleoperational medical system 100. In the pictured embodiment, the needle system 205 is manipulated (e.g., mechanically articulated or otherwise moved) by an actuator 210. In some embodiments, the actuator 210 may be controlled by a teleoperational platform 215 (e.g., the teleoperational platform 215 may send control signals to the actuator 210). The teleoperational platform 215 may include the teleoperational medical system 102 shown in FIG. 1. During the procedure, the teleoperational platform 215 may enable mechanical articulation and control of a variety of medical instruments in addition to the needle system 205, such as, by way of non-limiting example, tissue graspers, electrosurgical cautery probes, retractors, staplers, vessel sealers, endoscopes, scalpels, ultrasonic shears, and suction/irrigation instruments.

In the pictured embodiment, the medical instrument system 200 includes a flexible sheath 225. The flexible sheath 225 is a hollow conduit shaped and configured to slidably receive the needle system 205. In some embodiments, the flexible sheath 225 is a delivery instrument configured to deliver the needle system to a target location within the patient's body. In that regard, the flexible sheath 225 includes a lumen 230 extending from a proximal end 232 to a distal end 234. In some embodiments, the flexible sheath 225 may comprise a flexible bronchial instrument, such as a bronchoscope or bronchial catheter for use in examination, diagnosis, biopsy, or treatment of a lung. In some embodiments, flexible sheath 225 may comprise a flexible gastrointestinal instrument, such as an endoscope for use in examination, diagnosis, biopsy, or treatment of a gastrointestinal organ. The medical instrument system 200 is also suited for navigation and treatment of other tissues, via natural or surgically created connected passageways, in any of a variety of anatomical systems including the colon, the intestines, the kidneys, the brain, the heart, the circulatory system, or the like.

In some embodiments, the medical instrument system 200 may be used for non-teleoperational exploratory procedures or in procedures involving traditional manually operated medical instruments, such as endoscopy. In such instances, the actuator 210 may be controlled manually by an optional manual controller 220. In some embodiments, the optional manual controller 220 is the actuator 210 itself (e.g., a knob, handle, or grip for a rotating needle). In other embodiments, the optional manual controller 220 can be a handle(s), trigger(s), lever(s), grip(s), or any other user interface for providing control inputs to the actuator 210. The optional manual controller 220 may be connected to the actuator 210 in a direct mechanical linkage and/or via electronic control, and may communicate with the actuator 210 in a wired and/or wireless fashion.

The needle system 205 includes an elongate instrument 235 including a flexible portion 238 and rigid portion 240. In the pictured embodiment, the elongate instrument 235 comprises a steerable, flexible needle including a sharp needle tip 245 at the rigid portion 240 (described in further detail below with relation to FIG. 3). The needle 235 includes a lumen 246 (shown in FIG. 4) extending from a proximal end 248 to a distal end 249. In other embodiments, the needle system 205 includes another type of elongate instrument instead of a needle.

The needle system 205 includes a steerable stylet 260. In the pictured embodiment, the stylet 260 is shown extending through the lumen 246 of the needle 235. The lumen 246 of the needle 235 is shaped and configured to slidably receive the stylet 260. The structural relationship between the stylet 260 and the needle 235 is further described below in relation to FIG. 5. The stylet 260 extends from a proximal end 262 to a distal end 264. The stylet includes an elongate, flexible body 266 and a steerable portion 268. A sensor element 270 extends axially along a longitudinal axis LA of the body 266. In the pictured embodiment, the sensor element 270 extends into the steerable portion 268. In other embodiments, the sensor element 270 terminates proximal to the steerable portion 268.

The needle system 205 can be manipulated by the actuator 210. In particular, the stylet 260 can be manipulated by the actuator 210. In one example, the actuator 210 can manipulate the stylet 260 (and, thereby, the needle 235) by steering the steerable portion 268 of the stylet 260 along a desired surgical trajectory to a target location within the patient, changing the shape of the steerable portion 268, and/or changing the orientation of the steerable portion 268. The steerable portion 268 of the stylet 260 will be described in further detail below with respect to FIGS. 4 and 5.

The needle system 205 may also house cables, linkages, or other steering controls (not shown in FIG. 2) that extend between the actuator 210 and the stylet 260 to controllably bend or turn steerable portion 268 of the stylet 260. In some embodiments, the needle 235 can define one or more additional lumens through which other medical instruments, cables, linkages, and/or other steering controls may extend.

In embodiments in which the instrument system 200 is actuated by a teleoperational assembly, the actuator 210 may include drive inputs that couple to motorized drive elements of the teleoperational assembly. In embodiments in which the instrument system 200 is manually operated, the actuator 210 may include gripping features, manual actuators, and other components for manually controlling the motion of the instrument system.

In various embodiments, the needle system 205 can include any number of steerable, flexible needles and respective stylets, as indicated by optional needle 280 and the optional stylet 282 (along with any dedicated or shared actuation, control, sensing, and/or processing elements required for the additional needles).

As used herein, needles refer to a broad category of flexible needles with control inputs and/or ports at the base (i.e., outside the body of the patient) and distal regions meant for piercing or puncturing target tissue. Depending on the shape and mechanical properties of the needle, interaction forces between the needle and the patient anatomy (i.e., the target tissue and/or any intervening anatomy between the surgical entry point and the target tissue) can cause the needle to deflect, such that steering can be provided by simply applying rotation to the base of the needle. Alternatively or additionally, the needle 235 can be manipulated by the stylet 260 (and the actuator 210) to provide shaping and directionality. Steerable needles generally have a sufficiently high axial stiffness and a tip shape to allow them to puncture or penetrate tissue with minimal axial compression, as compared to catheter-type devices that have a low axial stiffness and are not suited to penetrate or puncture.

Figure 3C:
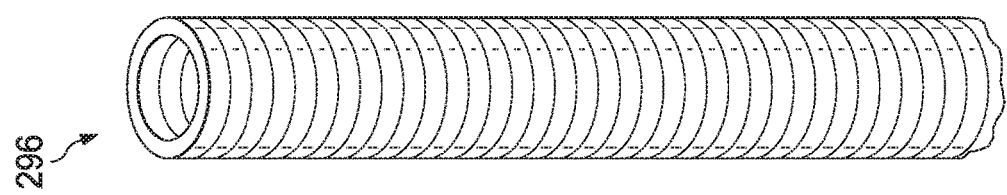
FIGS. 3A-3C illustrate perspective views of exemplary needle shafts in accordance with various embodiments of the present disclosure.
Figure 3B:
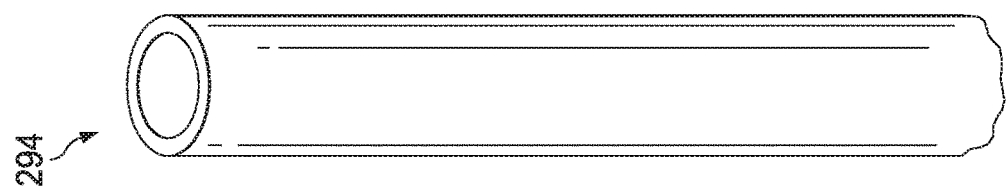
Figure 3A:
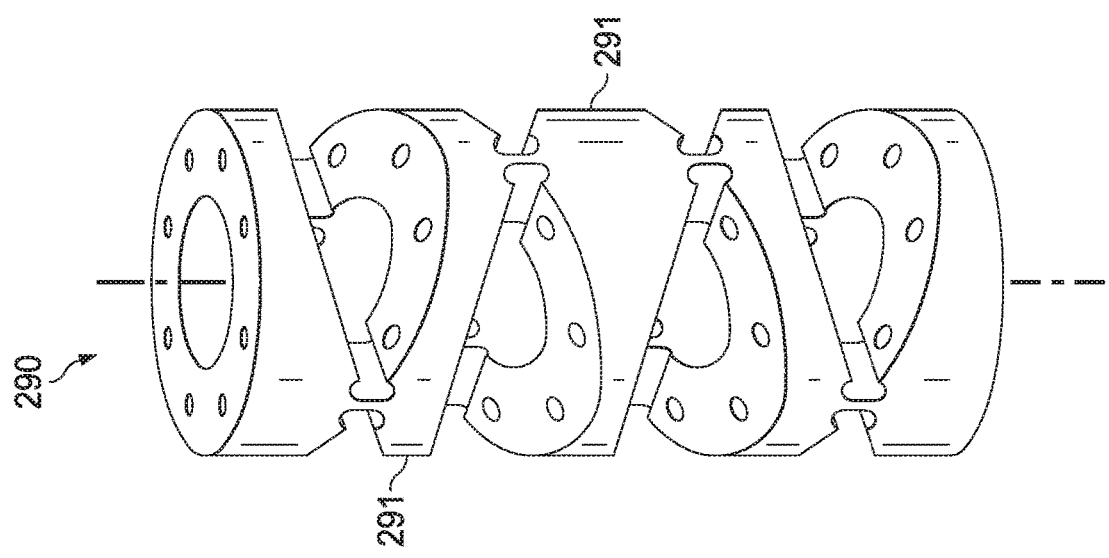

Note that the term "flexible" in association with the needle 235 should be broadly construed. In essence, it means the needle can be bent without harm. In some embodiments, as shown in FIG. 3A, a flexible needle 290 may include a series of closely spaced components 291 that are similar to "vertebrae" in a snake-like arrangement. For example, see U.S. Pat. No. 6,817,974 and U.S. Pat. App. Pub. No. 2013/0046317, both of which are incorporated herein by reference in their entirety. In such an arrangement, each component 291 is a short link in a kinematic chain, and movable mechanical constraints (e.g., pin hinge, cup and ball, and the like) between each link may allow one (e.g., pitch) or two (e.g., pitch and yaw) degrees of freedom (DOF) of relative movement between the links. In other embodiments, the needle 290 is continuous, such as a closed, elastomeric, bendable tube 294 as shown in FIG. 3B (e.g., Nitinol, polymer, and the like) or an open, bendable tube 296 as shown in FIG. 3C (e.g., kerf-cut tube, helical coil, and the like). In the embodiment shown in FIG. 3C, the tube 296 comprises a flexible length of material wound into a spiral or coiled configuration to form resiliently flexible tubular body. For example, the tube 296 may include features similar to that described in U.S. Pat. App. Pub. No. 2012/0123395, which is incorporated herein by reference in its entirety.

The flexible needle 290 may be made of any suitable biocompatible material that provides the requisite tensile and flexural properties. Suitable materials may include, by way of non-limiting example, shape memory material such as Nitinol, stainless steel, and plastics. In some embodiments, the flexible needle 290 is made from the same material throughout. In other embodiments, the flexible needle 290 may be made from two or more different materials. In some embodiments, the flexible needle 290 may be coated with a biocompatible lubricant.

Figure 4:
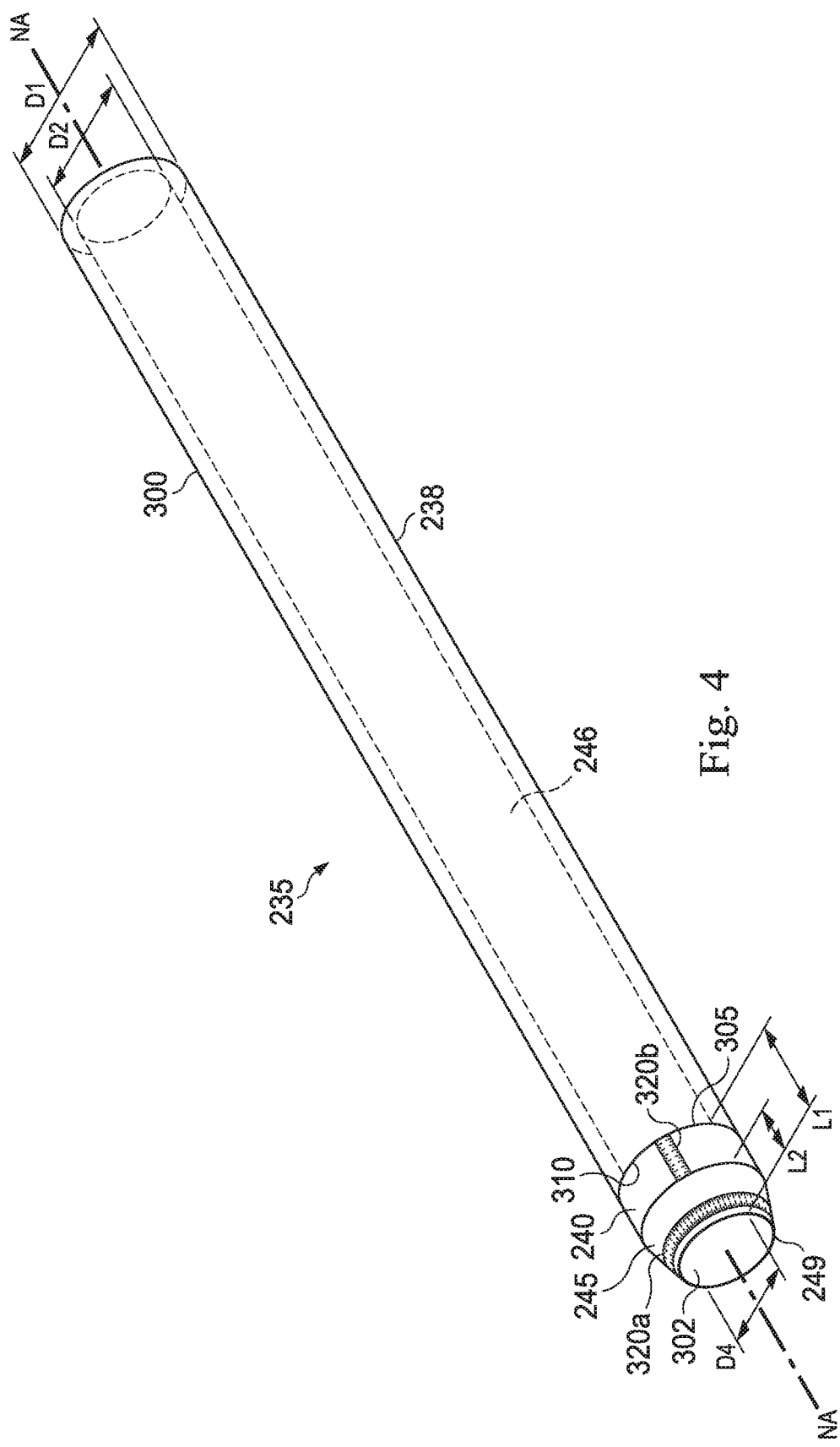
FIG. 4 illustrates a perspective view of an exemplary needle in accordance with an embodiment of the present disclosure.

FIG. 4 illustrates a distal portion 300 of the needle 235. As mentioned above in relation to FIG. 2, the needle 235 includes the flexible portion 238 and the rigid portion 240. The flexible portion 238 is proximal to the rigid portion 240. In the pictured embodiment, the flexible portion 238 comprises a hollow, continuous, flexible tube defining the lumen 246. As mentioned above, the flexible portion 238 may comprise a coiled structure that lends the needle 235 maximum flexibility in combination with desired column strength and minimal axial compression (as shown in FIG. 3C). The lumen 246 terminates at the distal end 249 of the needle 235. In the pictured embodiment, the flexible portion 238 is passively flexible and is configured to bend in response to external or internal forces. In other embodiments, the flexible portion 238 may be actively steerable (e.g., controllable by the actuator 210 shown in FIG. 2).

In the pictured embodiment, the rigid portion 240 includes the distal tip 245, which comprises the cutting element 245 or blade 245 of the needle 235. The distal tip 245 is configured to penetrate and sample tissue while allowing for a predictable curve path and needle steering through tissue. In the pictured embodiment, the distal tip 245 comprises an annular, non-beveled, partially conical blade. Unlike a beveled blade, the symmetrical, conical blade can core through tissue while maintaining a relative straight path. As the needle 235 is advanced through tissue, tissue can enter the lumen 246 through an aperture 302 at the distal end 249.

The rigid portion 240 and the flexible portion 238 are fixedly attached to one another by any of a variety of known methods, including by way of non-limiting example, adhesive, welding (e.g., laser-welding), and/or mechanical fasteners. For example, in the pictured embodiment, a distal end 305 of the flexible portion 238 is attached to a proximal end 310 of the rigid portion 240 by glue adhesive. In some embodiments, however, the rigid portion 240 can extend over the flexible portion 238 and attach to the flexible portion 238 at a more proximal location along the length of the proximal portion 238. In some embodiments, the rigid portion 240 is an integral extension of the flexible portion 238.

In the pictured embodiment, the needle 235 includes markers 320a, 320b. The marker 320a is positioned on the distal tip 245, and the marker 320b is positioned proximal to the distal tip 245 on the rigid portion 240. The markers 320a, 320b can function as insertion distance or positional indicators. In some embodiments, the markers 320a, 320b may be radiopaque (e.g., fluoroscopic markers). The marker 320a comprises a ring marker, and the marker 320b comprises a band marker. Other embodiments may include any number, type, and arrangement of positional markers.

The rigid portion 240, including the distal tip 245, has a length L1 ranging from approximately 1 mm to 10 mm. For example, in one embodiment, the rigid portion 240 has a length L1 of approximately 8 mm. Other lengths L1 of the rigid portion 240 may be larger or smaller. The distal tip 245 has a length L2 ranging from approximately 1 to 8 mm. For example, in one embodiment, the rigid portion 240 has a length L2 of approximately 4 mm. Other lengths L2 of the distal tip 245 may be larger or smaller. The above dimensions are provided for exemplary purposes only, and are not intended to be limiting. Other dimensions are contemplated.

The needle 235 has an outer diameter D1 ranging from approximately 1 mm to 2.5 mm. For example, in one embodiment, the needle 235 has an approximately 1.5 mm outer diameter. Other needle outer diameters may be larger or smaller. In some embodiments, the outer diameter D1 tapers from the proximal end 248 (shown in FIG. 2) to the distal end 249 of the needle 235, and the needle outer diameter D1 at the proximal end 248 is greater than the needle outer diameter D1 at the distal end 249. In some embodiments, the needle outer diameter D1 is substantially unchanged throughout the length of the needle 235. In alternative embodiments, there can be an abrupt change or stop in needle 235 between a larger outer diameter D1 of a proximal portion to a smaller outer diameter of the distal portion 300. The above dimensions are provided for exemplary purposes only, and are not intended to be limiting. Other dimensions are contemplated.

The needle 235 has an inner luminal diameter D2 ranging from approximately 0.8 mm to 1.4 mm. The inner diameter D2 is sized to allow the passage of tissue and fluid through the lumen 246. For example, in one embodiment, the needle 235 has an approximately 1 mm inner diameter D2. Other needle inner diameters may be larger or smaller. In some embodiments, the inner diameter D2 tapers from the proximal end 248 (shown in FIG. 2) to the distal end 249 of the needle 235, and the inner diameter D2 at the proximal end 248 is greater than the inner diameter at the distal end 249. In some embodiments, the inner diameter D2 is substantially unchanged throughout the length of the needle 235. In alternative embodiments, there can be an abrupt change or stop in needle 235 between a larger inner diameter D2 of a proximal portion to a smaller inner diameter of the distal portion 300. The above dimensions are provided for exemplary purposes only, and are not intended to be limiting. Other dimensions are contemplated.

Figure 5:
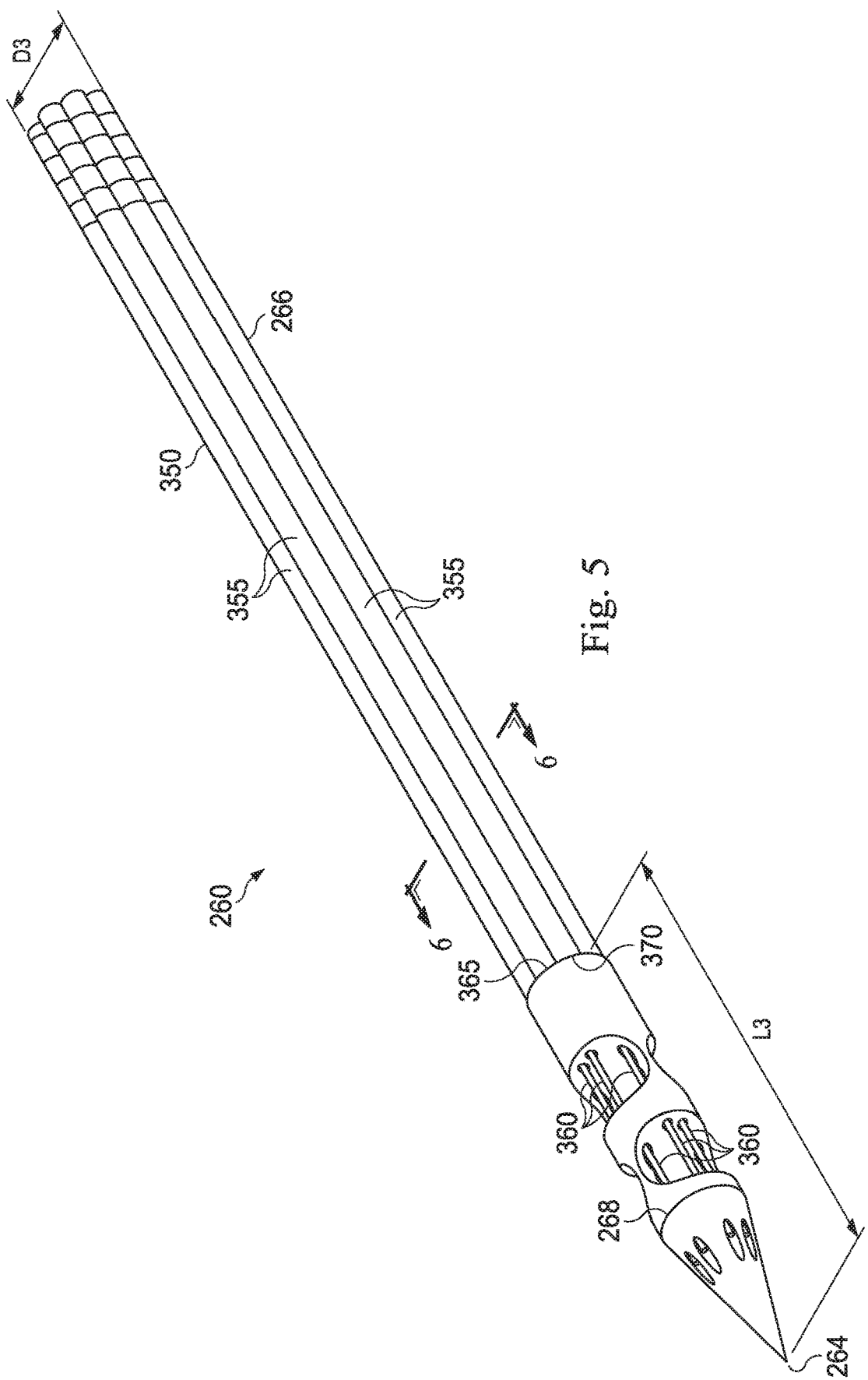
FIG. 5 illustrates a perspective view of an exemplary sensor stylet in accordance with an embodiment of the present disclosure.
Figure 6:
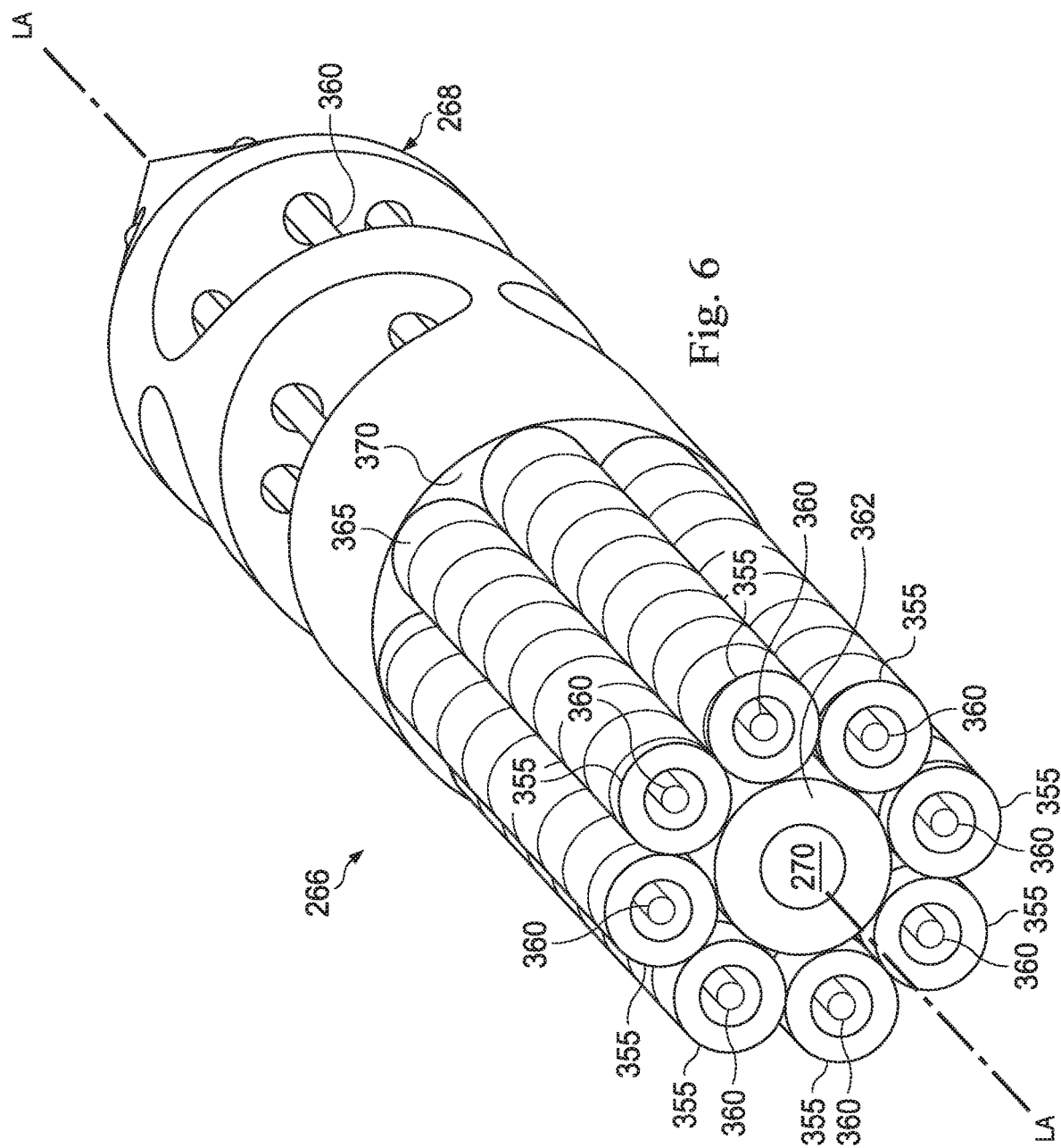
FIG. 6 illustrates perspective and partially cross-sectional view of a portion of the exemplary sensor stylet shown in FIG. 5 across the line 6-6 in accordance with an embodiment of the present disclosure.

FIG. 5 illustrates a perspective view of the steerable stylet 260 shown in FIG. 2. In particular, FIG. 5 illustrates a distal portion 350 of the stylet 260. As mentioned above with reference to FIG. 2, the stylet 260 includes the elongate, flexible body 266 and the steerable portion 268. In the pictured embodiment, the body 266 is configured to passively deflect in response to forces acting upon the flexible body, and the steerable portion 268 is configured to actively articulate in response to the teleoperational assembly and/or control signals from the actuator 210 (shown in FIG. 2). The body 266 is configured to carry and route actuation cables (e.g., actuation cables 360) to the steerable portion 268. In the pictured embodiment, the body 266 comprises multiple actuation conduits 355 bundled together to guide actuation cables 360 into the steerable portion 268. As shown in FIGS. 5 and 6, the body 266 lacks a solid wall surrounding the bundled conduits 355. In other embodiments, the body 266 may include a sheath surrounding the bundle of conduits 355.

The stylet 260 has an outer diameter D3 ranging from approximately 0.8 mm to 1.4 mm. For example, in one embodiment, the stylet 260 has an approximately 1.0 mm outer diameter. Other stylet outer diameters may be larger or smaller. In the pictured embodiment, the outer diameter at the proximal end 262 (shown in FIG. 2) is greater than the outer diameter at the distal end 264. In some embodiments, the outer diameter D3 of the stylet 260 closely approximates an inner diameter D4 (shown in FIG. 4) of the distal tip 245 of the needle 235 such that the distal tip 245 of the needle 235 is configured to snugly receive the steerable portion 268 of the stylet 260. In some embodiments, the inner diameter D4 is approximately equal to the inner diameter D2. In some embodiments, the outer diameter D3 of the stylet 260 closely approximates the inner diameter D2 of the needle 235 such that the sensor element 270 is substantially aligned with the longitudinal axis NA of the needle 235 (shown in FIG. 4) when the stylet 260 is received within the lumen 246 of the needle 235. In some embodiments, the outer diameter D3 of the stylet 260 closely approximates the inner diameter D2 of the needle 235 such that the stylet 260 blocks the lumen 246 of the needle 235 when the stylet 260 is received within the lumen 246.

In particular, the outer diameter D3 remains constant throughout the length of the body 266, and tapers distally along at least a portion of a length L3 of the steerable portion 268. In alternative embodiments, the stylet outer diameter D3 varies along the length of the stylet 260. In alternative embodiments, there can be an abrupt change or stop in stylet 260 between a larger outer diameter of a proximal portion of the stylet 260 to a smaller outer diameter of the distal portion 350. The length L3 of the steerable portion 268 can range from approximately 2 to 6 mm. For example, in one embodiment, the steerable portion 268 has a length L3 of approximately 5 mm. Other lengths L3 of the steerable portion 268 may be larger or smaller. The above dimensions are provided for exemplary purposes only, and are not intended to be limiting. Other dimensions are contemplated.

FIG. 6 illustrates a perspective and partially cross-sectional view of the body 266 of the stylet 260. As shown in FIG. 6, each conduit 355 of the body 266 comprises a flexible tube configured to slidably receive an actuation cable 360. In the pictured embodiment, each conduit 355 comprises a flexible microcoil structure. In other embodiments, each conduit 355 may comprise any suitable type of hollow, flexible, biocompatible tube sized and configured to slidably receive the actuation cable 360. In the pictured embodiment, the body 266 includes eight conduits 355 arranged circumferentially around a sensor conduit 362 configured to carry the sensor element 270. In the pictured embodiment, each conduit 355 is positioned around the sensor conduit 362 immediately adjacent a neighboring conduit 355 so as to leave no gaps (e.g., radially) between the conduits 355. In one aspect, the sensor conduit 362 is shaped and configured to maintain the axial position of the sensor element 270 within a range of 1 mm (relative to the longitudinal axis LA of the stylet 260). The conduits 355 and the sensor conduit 362 are fixedly attached to one another by any of a variety of known methods, including by way of non-limiting example, adhesive, welding (e.g., laser-welding), and/or mechanical fasteners. For example, in the pictured embodiment, the conduits 355 are coupled to each other and to the sensor conduit 360 by laser-welding. This configuration can lend the stylet 260 a desired degree of axial stiffness with a small pitch and little to no axial compression. The body 266 may comprise any number and arrangement of conduits 355 configured to accurately route the desired number of actuation cables 360 into the steerable portion 268. For example, in the pictured embodiment, because the steerable portion 268 is configured to receive eight actuation cables 360, the body 266 includes eight conduits 355 with each conduit 355 configured to receive an individual actuation cable 360. In such embodiments, the pulling or actuation of the actuation cables 360 contributes largely to the bending of the stylet tip (i.e., the steerable portion 268), which may improve controllability of the device shape, position, and direction of advancement. Some other embodiments may lack conduits for housing actuation cables. In such embodiments, tensioning or pulling the actuation cables may produce a distributed bending along the entire stylet 260.

As shown in FIGS. 5 and 6, the body 266 and the steerable portion 268 are fixedly attached to one another by any of a variety of known methods, including by way of non-limiting example, adhesive, welding (e.g., laser-welding), and/or mechanical fasteners. For example, in the pictured embodiment, a distal end 365 of the body 266 is coupled to a proximal end 370 of the steerable portion 268 by laser-welding. In some embodiments, however, the proximal end 370 can extend over the distal end 355 of the body 266 and attach to the body 266 at a more proximal location along the length of the body. In such embodiments, the body 266 may extend a small distance into the steerable portion 268. In some embodiments, the steerable portion 268 is an integral extension of the body 266.

As shown in FIGS. 2 and 6, the sensor element 270 extends axially along a longitudinal axis LA of the body 266. In the pictured embodiment in FIG. 6, the sensor element 270 extends through the center of the body 266 within the sensor conduit 362. In other embodiments, the sensor conduit 362 could be positioned in an off-center position relative to the conduits 355. In the pictured embodiment, the sensor element 270 extends at least partially into the steerable portion 268 of the stylet 260. In alternative embodiments, the sensor element 270 terminates within the body 266, proximal to the steerable portion 268.

If the needle system 205 is the medical instrument system 104 of the teleoperational medical system 100 shown in FIG.

1, the sensor element 270 may be a component of the sensor system 108. If the needle system 205 is manually operated or otherwise used for non-robotic procedures, the sensor element 270 may be coupled to a tracking system that interrogates the sensor element 270 and processes the received data (e.g., shape data from a shape sensor element). Regardless of the specific steering mechanism of the stylet 260, the usability of the needle system 205 is enhanced by the inclusion of the sensor element 270. Depending on how far into the steerable portion 268 the sensor element 270 extends, the sensor element 270 can determine the position, orientation, speed, pose, and/or shape of the steerable portion 268 of the stylet 260 and/or of one or more discrete segments along the stylet body 266 and/or the needle 235. The data read by the sensor element 270 can be converted into useable shape and/or positional information by the sensor system 108 and/or the control system 112 shown in FIG. 1. The shape and/or positional information can then be used to guide further manipulation of the stylet 260 (and, consequently, the needle 235).

In the pictured embodiment, the sensor element 270 is a sensor that provides shape and/or position measurements of the stylet 260 (and the needle 235, when the stylet 260 is positioned within the needle 235). In the pictured embodiment, the sensor element 270 may comprise an EM sensor system that can be used for point localization (i.e., position/orientation measurement). In some embodiments, the sensor element 270 includes multiple EM sensors or a single EM sensor cumulatively measured at various time intervals to determine the shape of the stylet 260 at any given point in time. The EM sensor element 270 may include one or more conductive coils that may be subjected to an externally generated electromagnetic field. Each coil of the EM sensor element 270 then produces an induced electrical signal having characteristics that depend on the position and orientation of the coil relative to the externally generated electromagnetic field. In one embodiment, the EM sensor system may be configured and positioned to measure six degrees of freedom ("6-DOF"), e.g., three position coordinates X, Y, Z and three orientation angles indicating pitch, yaw, and roll of a base point. In an alternative embodiment, the EM sensor system may be configured and positioned to measure five degrees of freedom ("5-DOF"), e.g., three position coordinates X, Y, Z and two orientations of a base point. For example, in some embodiments, the sensor element 270 comprises a 5-DOF EM sensor configured to provide position and/or orientation data related to the body 266 of the stylet 266 (e.g., to allow the user to recognize where the needle tip 249 is within the patient as the needle 235 is extended over and along with the stylet 260). Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

In some embodiments, the sensor element 270 may include an optical fiber aligned with the stylet 260 (e.g., the optical fiber may be provided within the sensor conduit 362 as shown in FIG. 6). The optical fiber of the sensor element 270 may form a fiber optic bend sensor for determining the shape of at least a portion of the needle system 205. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the needle system 205 may be determined using other techniques.

More specifically, light passing through the optical fiber is processed to detect the shape of the stylet 260 and/or needle system 205 and for utilizing that information to assist in medical procedures. The sensor system (e.g., the sensor system 108 or another type of tracking system as described in FIG. 2) may include an interrogation system for generating and detecting the light used for determining the shape of the stylet 260. This information, in turn, can be used to determine other related variables, such as velocity and acceleration of the parts of the medical instrument.

As described above, the sensor element 270 may comprise an elongate fiber optic shape sensor that provides shape measurements along the length of the stylet 260. The sensor element 270 may include a single continuous sensing region over the length of the sensor or multiple sensing regions distributed along the length of the sensor. In contrast to a discrete position sensor, an elongate sensor enables shape measurements along the length of the stylet 260 with a single sensor. The integrated nature of a single elongate shape sensor may provide more accurate shape measurement of the stylet 260, which enables more precise control and/or enhanced error correction to ensure that the stylet 260 (and needle 235) accurately traverses a desired surgical trajectory.

Note that although the sensor element 270 is depicted and described as a single elongate sensor for explanatory purposes, in other embodiments the sensor element 270 can include multiple discrete shape sensors. In one such embodiment, each shape sensor may measure the shape of a continuous portion of the overall length of the stylet 260. Multiple shape sensors may provide greater shape modeling accuracy or may be useful in compensating for environmental factors that can affect the sensors (e.g., temperature variations along the length of the stylet 260).

FIGS. 7A and 7B illustrate the steerable portion 268 of the stylet 260 according to one embodiment of the present disclosure. The stylet 260 generally has a high axial stiffness and a tip shape (i.e., the shape of the steerable portion 268) that allows it to puncture or penetrate tissue with minimal axial compression or buckling, as compared to catheter-type devices that have a low axial stiffness and are not well suited to penetrate or puncture. In the pictured embodiment depicted in FIG. 7A, the steerable portion 268 comprises a flexible, jointed structure that tapers toward the distal end 264. The steerable portion 268 extends from a proximal end 400 to the distal end 264. In the pictured embodiment, the steerable portion 268 comprises a proximal bendable section 410 and a distal bend-resistive section 415. In the pictured embodiment, the bendable section 410 comprises a continuous, jointed structure including a plurality of articulable segments: a proximal segment 417, a middle segment 418, and a distal segment 419. A proximal joint pivot 420 separates the proximal segment 417 and the middle segment 418, and a distal joint pivot 425 separates the middle segment 418 and the distal segment 419. The bendable section 410 shown in FIG. 7 is illustrative only and is not intended to be limiting. In view of this disclosure, the bendable section 410 may comprise any type of steerable, generally tubular structure configured to house the actuation cables 360 and to bend in multiple directions upon actuation of the actuation cables 360. In other words, the steerable portion 268 of the stylet 260 may include from at least one bendable section having any number of segments to whatever number of bendable sections is needed to provide the required functionality of the steerable stylet 260. In some instances, the steerable portion 268 of the stylet 260 includes components or features similar to those disclosed in U.S. Patent Application No. 2005/0273085, entitled "Articulating mechanism with flex-hinged links" and filed on Sep. 24, 2004, and/or U.S. Patent Application No. 2013/0046317, entitled "Medical instrument with flexible wrist mechanism" and filed on Aug. 15, 2011, both of which are hereby incorporated by reference in their entirety.

The steerable portion 268 may be made of any suitable biocompatible material that provides the requisite tensile and flexural properties. Suitable materials may include, by way of non-limiting example, a polymer, shape memory material such as Nitinol, stainless steel, and plastics. In some embodiments, the steerable portion 268 is made from the same material throughout. In other embodiments, the steerable portion 268 may be made from two or more different materials. For example, in some embodiments, the bend-resistive section 415 may be formed of a more rigid material than the bendable section 410. In some embodiments, the steerable portion 268 may be coated with a biocompatible lubricant.

The bendable section 410 and the bend-resistive section 415 are fixedly attached to one another by any of a variety of known methods, including by way of non-limiting example, adhesive, welding (e.g., laser-welding), and/or mechanical fasteners. For example, in the pictured embodiment, the distal segment 419 of the bendable section 410 and the bend-resistive section 415 are coupled to each other by laser-welding. In other embodiments, the bendable section 410 and the bend-resistive section 415 may be formed from a single, unitary, elongate tubular or solid member which may be cut according to the invention to form the three segments 417, 418, 419, the proximal joint pivot 420, and the distal joint pivot 425 of the bendable section 410 and the bend-resistive section 415.

The bend-resistive section 415 forms the distal tip of the stylet 260, and is shaped and configured to penetrate tissue with minimal axial compression. In the pictured embodiment, the bend-resistive section 415 forms a conical, sharp tip. In other embodiments, the bend-resistive section 415 may have any shape that enables it to penetrate tissue with minimal axial compression. The bend-resistive section 415 is configured to receive and/or anchor the actuation cables 360. In the pictured embodiment, the bend-resistive section 415 includes grooves or indentations 430 to receive and/or anchor distal ends 435 of the actuation cables 360. In the pictured embodiment, the stylet 260 includes eight actuation wires 360, and the bend-resistive section 415 includes eight complementary grooves 430 to receive each of the actuation wires 360. In other embodiments, the bend-resistive section 415 may include any number of grooves 430 to accommodate the number of actuation wires 360 included in the stylet 260. In the pictured embodiment, the grooves 430 are arranged symmetrically and circumferentially around the bend-resistive section 415. In other embodiments, the grooves 430 may be arranged in any fashion about the bend-resistive section 415 that enables the desired steerability of the stylet 260.

As mentioned above, the steerable portion 268 (and, in particular, the bendable section 410) is configured to actively articulate upon selective actuation of individual actuation cables 360 in response to the teleoperational assembly and/or control signals from the actuator 210 (shown in FIG. 2). As shown in FIG. 7A, each actuation cable 360 extends from the flexible portion 266 into and through an individual channel 440 in the steerable portion 268 before terminating within the grooves 430. In the pictured embodiment, four actuation cables 360a, 360b, 360c, and 360d are shown. For example, the pictured embodiment shows the distal ends 435a, 435b, 435c, and 435d of the actuation wires 360a, 360b, 360c, and 360d, respectively, anchored within four complementary grooves 430.

In the pictured embodiment, the actuation cables 360 are arranged in pairs about a longitudinal axis LA of the stylet 260. In particular, as shown in FIG. 7A, the actuation cable 360a and the actuation cable 360b form a pair extending through the channels 440a and 440b. In one embodiment, the actuation cable 360a and 360b are two branches of the same continuous actuation cable, and the two branches 360a, 360b are actuated together at the proximal end. FIG. 7B illustrates a cross-sectional view of a segment 217 of the steerable portion 268 (as shown in FIG. 2). As shown in FIG. 7B, the channels 440 are grouped into four pairs arranged symmetrically about the longitudinal axis LA of the steerable portion 268. For example, the channel 440a is paired with the channel 440b, and the channel 440c is paired with the channel 440d. Thus, the actuation cable 360a is paired with the actuation cable 360b, and the actuation cable 360c is paired with the actuation cable 360d. In other embodiments, the channels 440 (and, consequently, the actuation cables 360) may be arranged in any fashion about the bendable section 410 that enables the desired steerability of the stylet 260.

Tension and/or extension forces can be applied to cause desired bending of the steerable portion 268 of the stylet 260. The actuation cables 360 can be controlled via mechanical tensioners, motor actuators, or any other mechanism (e.g., coupled to the stylet 260). For example, in some embodiments, the actuation cables 360 can include material that responds to thermal changes, such as Nitinol wire(s) configured to contract in response to electrical current-induced heating (such as described in "A Nitinol Wire Actuated Stewart Platform", by Dunlop et al. (Proc. 2002 Australasian Conference on Robotics and Automation, Nov. 27-29, 2002), herein incorporated by reference in its entirety). Various other steering mechanisms will be readily apparent. For example, in some embodiments, each actuation cable 260 may extend through one of the plurality of actuation conduits, into a channel 440, and return through another of the plurality of actuation conduits.

In FIG. 7A, the steerable portion 268 is shown in a straight or unbent condition with the longitudinal axis LA in parallel alignment with an illustrative x-axis. FIGS. 8A and 8B illustrate the steerable portion 268 in bent conditions. In FIG. 8A, because the actuation cables 360c and 360d are in a tensioned condition, the steerable portion 268 bends (e.g., in pitch) at the proximal joint pivot 420 toward the direction of the channels 440c and 440d in the illustrative x-z plane. In particular, the parts of the steerable portion 268 distal to the proximal joint pivot 420 (i.e., the segment 418, the segment 419, and the bend-resistive section 415) bend or articulate in the direction of the channels 440c and 440d carrying the tensioned cables 360c and 360d, respectively. In FIG. 8B, because the actuation cables 360a and 360b are also in a tensioned condition (i.e., in addition to the actuation cables 360c and 360d), the steerable portion 268 also bends at the distal joint pivot 425 toward the direction of the channels 440a and 440b in the illustrative x-y plane. In particular, the parts of the steerable portion 268 distal to the distal joint pivot 425 (i.e., the segment 419 and the bend-resistive section 415) bend or articulate in the direction of the channels 440a and 440b carrying the tensioned cables 360a and 360b, respectively.

FIG. 9 illustrates a perspective view of the needle system 500 according to one embodiment of the present disclosure. The needle system 500 may be similar to the needle system 205 shown in FIG. 2. In particular, FIG. 9 illustrates the exemplary sensor stylet shown in FIG. 5 positioned within and extending from the exemplary needle shown in FIG. 4 according to the present disclosure. The needle system 500 includes the stylet 260, which is slidably positioned within the lumen 246 of the needle 235. The stylet 260 and the needle 235 are arranged in a telescoping fashion relative to each other. Thus, the stylet 260 can retract completely into the lumen 246 of the needle 235 and can also extend distally from the needle 235 (i.e., while the needle 235 remains stationary), as shown in FIG. 9.

As depicted in FIG. 9, the stylet 260 is shaped and sized to be received inside the needle 235. In particular, the steerable portion 268 of the stylet 260 is shaped and sized to be snugly received inside the rigid portion 240 of the needle 235. In the pictured embodiment, the inner diameter D2 of the needle 235 is sized to be only slightly larger than the outer diameter D3 of the stylet 260, thereby allowing the stylet 260 to be securely supported within rigid portion 240 of the needle 235 as it emerges from the needle 235.

In some embodiments, the teleoperational medical system 100 shown in FIG. 1 is configured to control the movement or articulation of the steerable portion 268 of the stylet 260. In particular, the teleoperational system 100 can control the actuation of the actuation cables 360 and thereby control the movement and bending of the steerable portion 268 of the stylet 260. If the steerable portion 268 is positioned within the needle 235 (as shown in FIG. 9) as the steerable portion 268 is manipulated or moved, then the needle 235 will mimic the movement of and move in unison with the steerable portion 268 (e.g., because the needle 235 sheathes and surrounds the moving part of the stylet 260). In some embodiments, the teleoperational system 100 and the needle system 500 are configured to shift the steerable portion 268 into a predefined set of shapes or bend angles. For example, in some embodiments, the steerable portion 268 may have a pre-defined first position with a "left-bend" having a preset angle αl at the proximal joint pivot 420 as shown in FIG. 8A by inputting a single command into the teleoperational system 100. In other embodiments, the steerable portion 268 may be manipulated and moved into a variety of bent shapes involving one or more joint pivots having a range of bend angles.

FIGS. 10-12 illustrate diagrammatic views of the exemplary needle system 500 shown in FIG. 9 navigating patient anatomy P to obtain a biopsy sample according to one embodiment of the present disclosure. FIG. 10 illustrates a diagrammatic view of the needle system 500 navigating a tortuous pathway 510 (i.e., a passageway within a patient's anatomy) with the stylet 260 in a retracted or sheathed condition within the needle 235 in accordance with an embodiment of the present disclosure. In the pictured embodiment, the needle system 500 is shown advancing through a flexible sheath 520 toward a target area 515. The flexible sheath 520 may be the same as the flexible sheath 225 described above in relation to FIG. 2. In the pictured embodiment, the needle 235 is slidably received within the flexible sheath 520, and the stylet 260 is slidably received within the needle 235. While the needle 235 is advanced through the flexible sheath 520, the stylet 260 is in a retracted or nonextended condition within the lumen 246 of the needle 235. In particular, the distal end 264 of the stylet 260 is positioned proximal to the distal end 249 of the needle 235. During advancement of the needle system 500 through the flexible sheath 520, the user need not utilize the sensor element 270 with the stylet 260, but the user may do so to confirm the accurate progression of the needle system 500 through the flexible sheath 520.

FIG. 11 illustrates a diagrammatic view of the needle system 500 steering toward the target area 515 in accordance with an embodiment of the present disclosure. In particular, FIG. 11 illustrates the stylet 260 emerging from the needle 235 to penetrate tissue in the direction of the target area 515. As the user advances the needle 235 from the flexible sheath 520, and throughout the procedure, the user may employ fluoroscopy or other imaging in cooperation with the radiopaque marker 320a (or other radiopaque markers, not pictured) to track the position of the needle 235 within the patient's anatomy (e.g., relative to the target area 515). After advancing the needle 235 and the stylet 260 from the flexible sheath 520 (i.e., with the stylet 260 positioned within the needle 235), the user can advance the stylet 260 from the needle 235 to penetrate tissue (e.g., without coring the tissue and while blocking the lumen 246 of the needle 235 from receiving tissue) ahead of the needle 235. As the sensor stylet 260 is advanced, the user may utilize data received from the sensor element 270 to evaluate and track the position, orientation, and progression of the stylet 260.

The information obtained from the sensor element 270 can be used in various ways. For example, from the measured shape the total insertion depth into the tissue as well as the tip position and orientation (e.g., the distal end 264 of the stylet 260) can be determined. These variables can be used in a servo-loop to precisely control insertion and orientation of the stylet 260 and needle 235—instead of measuring just the proximal insertion and rotation amounts on the control inputs and assuming perfect transfer to the tip, the sensor element 270 can be used to directly measure the distal insertion and rotation, independent from the torsional and axial flexibility of the needle 235 or the stylet 260 and the effects of friction and normal forces between the needle 235 or the stylet 260 and the tissue. In another embodiment, the measured tip position and orientation (as computed from the shape information) can be used in planning algorithms that compute feasible paths from the current stylet position to the target area 515. The sensor element 270 can be used to measure the sensor stylet pose and needle pose in place of or in addition to (potentially imprecise) imaging techniques.

In another embodiment, the sensor element 270 can be used in conjunction with imaging techniques to improve registration of the needle 235 and/or the stylet 260 relative to preoperative data. The base, or some other portion of the sensor element 270 and/or the sensor stylet 270, can be registered to the image coordinate space by attaching an imagable fiducial feature to a portion of the sensor element 270, or docking a fixed reference point on the sensor element 270 to a visible fiducial feature on the patient, for example. The intraoperative imaging would provide a means to adapt stylet and needle trajectory in response to tissue motion or deformation. The measured shape of the stylet 260 and/or the needle 235 could be used to assist in detecting and localizing the stylet 260 and/or the needle 235 in intraoperative images, such that its position/orientation with respect to anatomical targets could be measured.

Based on the sensed data and subsequent conclusions from the sensor element 270 of the stylet 260, the user and/or the teleoperational system 100 can selectively steer the steerable portion 268 of the stylet 260 towards the target area 515 (e.g., by selectively tensioning or relaxing particular actuation cables 360, shown in FIG. 5, to bend particular sections of the steerable portion 268, as shown in FIGS. 8A and 8B). In particular, the sensor element 270 of the stylet 260 can be used, in conjunction with a driving mechanism, to provide input in order to manually (e.g., by the user) or automatically (e.g., by the teleoperational system 100) control the actuator that steers the steerable portion 268 of the stylet 260 during a medical procedure.

As or after the user advances the stylet 260 into the tissue, the user may distally advance the needle 235 to slide the needle 235 over the stylet 260. FIG. 12 illustrates the rigid portion 240 of the needle 235 extending over the steerable portion 268 of the stylet 260 (and following the curvature of the stylet 260) to penetrate the target area 515 (e.g., to obtain or aspirate a biopsy sample from the target area 515). As the stylet 260 is steered precisely to the target area 515 (or even to a discrete region of interest within the larger target area 515), the stylet 260 can be advanced slightly ahead of the needle 235 to guide the trajectory of the needle 235 as the needle 235 advances over the stylet 260 through the tissue.

After the user confirms (e.g., using radiographic data and/or sensed data from the sensor element 270) the accurate positioning of the needle 235 within the target area, the user may proximally withdraw the stylet 260, as shown in FIG. 13, and begin aspirating and/or coring through the target area 515 to obtain a tissue sample (e.g., a biopsy sample). In some embodiments, the needle system 500 aspirates a biopsy sample of the target area 515 into the needle lumen 246. In other embodiments, the needle system 500 cores a biopsy sample of the target area 515 into the rigid portion 240 of the needle 235.

FIG. 14 illustrates one embodiment of a method for using or controlling the stylet 260 in a flowchart 600. At step 605, the needle system 500 (e.g., the stylet 260 and the needle 235) may be advanced together within patient anatomy (e.g., the patient anatomy P shown in FIG. 10) in the direction of a region of interest or target tissue (e.g., the target area 515 shown in FIG. 10), as shown in FIG. 10. In some embodiments, the stylet 260 and the needle 235 may be advanced within a delivery device (e.g., the flexible sheath 520 shown in FIG. 10). As the stylet 260 and the needle 235 are advanced toward the region of interest, the stylet 260 may be telescopically sheathed within the needle 235.

At step 610, during advancement of the needle system 500 toward the region of interest, the sensor element 270 of the stylet 260 need not be utilized, but the control system 112 (e.g., a processor of the control system 112) may analyze the shape and/or positional data supplied by the sensor element 270 to confirm the accurate progression of the needle system 500 through the patient anatomy.

At step 615, after the needle system 500 is positioned in the vicinity of the region of interest, the stylet 260 may be advanced ahead of the needle 235 (e.g., past the distal end 249 of the needle 235) to penetrate tissue, as shown in FIG. 11. The stylet 260 may penetrate the tissue without coring the tissue and facilitate the later progress of the needle 235 through the tissue.

At step 620, the sensor element 270 can acquire or detect the current shape/position of the stylet 260 as it is advanced into the tissue, and the control system 112 may analyze the shape and/or positional data supplied by the sensor element 270 to determine the position of the needle system 500 relative to the region of interest.

At step 625, the control system 112 may steer the stylet 260 toward to the region of interest based on the shape and/or positional data supplied by the sensor element 270.

At step 630, the control system 112 may advance the needle 235 over the stylet 260 toward or into the region of interest, as shown in FIG. 12.

At step 635, the stylet 260 may be withdrawn through the needle 235, as shown in FIG. 13.

At step 640, the needle 235 may be advanced further into the region of interest to core through the tissue and to obtain a biopsy sample.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A minimally invasive system comprising:
    an elongate instrument extending from a proximal end to a distal end and including:
        a flexible proximal portion;
        a rigid distal portion, the flexible proximal portion fixedly coupled to the rigid distal portion; and
        a lumen extending from the proximal end to the distal end through the flexible proximal portion and the rigid distal portion and defining a longitudinal axis of the elongate instrument; and
    a stylet slidably disposed within the lumen of the elongate instrument, the stylet including a flexible body fixedly coupled to a steerable portion and a sensor extending through the flexible body, the stylet being movable within the elongate instrument between a retracted condition in which the steerable portion is retracted within the elongate instrument and an extended configuration in which the steerable portion at least partially extends from the rigid distal portion of the elongate instrument, wherein a plurality of actuation cables extend through the flexible body of the stylet and terminate in the steerable portion of the stylet, and wherein the steerable portion of the stylet comprises a bend-resistive section and a bendable section, the bendable section including:
a plurality of articulable segments linked by the plurality of actuation cables; and
a plurality of joint pivots disposed between adjacent articulable segments.

2. The minimally invasive system of claim 1, wherein the sensor is configured to measure a shape of at least a portion of the stylet.

3. The minimally invasive system of claim 1, wherein the sensor is configured to measure a position of at least a portion of the stylet.

4. The minimally invasive system of claim 1, wherein the sensor extends into the steerable portion of the stylet.

5. The minimally invasive system of claim 1, wherein the stylet includes an outer diameter that closely approximates an inner diameter of the elongate instrument such that the stylet blocks the lumen of the elongate instrument when the stylet is received within the lumen of the elongate instrument.

6. The minimally invasive system of claim 1, wherein the stylet includes a sensor conduit configured to maintain an axial position of the sensor in substantially parallel alignment with a longitudinal axis of the elongate instrument.

7. The minimally invasive system of claim 1, further including a plurality of actuation conduits within the flexible body of the stylet and a plurality of actuation channels within the steerable portion of the stylet, wherein each of the plurality of actuation cables extend through a discrete actuation conduit of the plurality of actuation conduits and anchor within a discrete actuation channel of the plurality of actuation channels.

8. The minimally invasive system of claim 7, wherein each actuation conduit comprises a flexible microcoil.

9. The minimally invasive system of claim 7, wherein the bend-resistive section further includes a plurality of grooves, wherein each groove of the plurality of grooves is configured to receive a corresponding actuation cable of the plurality of actuation cables.

10. The minimally invasive system of claim 7, wherein each actuation conduit of the plurality of actuation conduits is positioned immediately adjacent a neighboring actuation conduit of the plurality of actuation conduits.

11. The minimally invasive system of claim 10, wherein the stylet includes a sensor conduit configured to maintain an axial position of the sensor in substantially parallel alignment with a longitudinal axis of the elongate instrument, and the plurality of actuation conduits are arranged circumferentially around the sensor conduit.

12. The minimally invasive system of claim 1, wherein each of the plurality of actuation cables maintains its radial position relative to the longitudinal axis of the stylet as each of the plurality of actuation cables extends from the flexible body into the steerable portion.

13. The minimally invasive system of claim 1, wherein a first joint pivot of the plurality of joint pivots is positioned between a first articulable segment and a second articulable segment, and wherein a second joint pivot of the plurality of joint pivots is positioned between the second articulable segment and a third articulable segment.

14. The minimally invasive system of claim 13, wherein the first joint pivot allows the first articulable segment to bend in a first plane relative to the second articulable segment, and the second joint pivot allow the second articulable segment to bend in a second plane relative to the third articulable segment, the first plane being different than the second plane.

15. The minimally invasive system of claim 14, wherein the first articulable segment is configured to bend to a predefined bend angle.

16. The minimally invasive system of claim 1, wherein the rigid distal portion of the elongate instrument comprises a partially conical, non-beveled, and annular cutting tip.

17. The minimally invasive system of claim 1, wherein the plurality of actuation cables are configured to anchor within the bend-resistive section of the steerable portion of the stylet.

18. The minimally invasive system of claim 17, wherein the bend-resistive section further includes a plurality of grooves, and wherein each actuation cable of the plurality of actuation cables is configured to anchor within a corresponding groove of the plurality of grooves.

19. The minimally invasive system of claim 1, wherein the bend-resistive section of the steerable portion of the stylet is distal to the bendable section of the steerable portion of the stylet.

20. The minimally invasive system of claim 1, wherein a distal end of the stylet comprises the steerable portion.

* * * * *

UNITED STATES PATENT AND TRADEMARK OFFICE
CERTIFICATE OF CORRECTION

PATENT NO. : 10,779,803 B2
APPLICATION NO. : 15/127811
DATED : September 22, 2020
INVENTOR(S) : Prisco et al.

Page 1 of 1

It is certified that error appears in the above-identified patent and that said Letters Patent is hereby corrected as shown below:

On the Title Page

Item (72), Line 2, Inventors:
Correct the Inventor city from "Leghorn" to -- Livorno --

Signed and Sealed this
Eighth Day of December, 2020

Andrei Iancu
*Director of the United States Patent and Trademark Office*